US012727817B2

(12) United States Patent
Chaiwala

(10) Patent No.: US 12,727,817 B2
(45) Date of Patent: Sep. 8, 2026

(54) INTELLIGENT AROMATHERAPY SYSTEM

(71) Applicant: Sonny Chaiwala, Ottawa (CA)

(72) Inventor: Sonny Chaiwala, Ottawa (CA)

(*) Notice: Subject to any disclaimer, the term of this patent is extended or adjusted under 35 U.S.C. 154(b) by 1281 days.

(21) Appl. No.: 17/541,476

(22) Filed: Dec. 3, 2021

(65) Prior Publication Data

US 2022/0175313 A1 Jun. 9, 2022

Related U.S. Application Data

(60) Provisional application No. 63/121,439, filed on Dec. 4, 2020.

(51) Int. Cl.

| | |
|---|---|
| *A61B 5/00* | (2006.01) |
| *A61B 5/01* | (2006.01) |
| *A61B 5/021* | (2006.01) |
| *A61B 5/024* | (2006.01) |
| *A61B 5/08* | (2006.01) |
| *A61B 5/11* | (2006.01) |
| *A61B 5/16* | (2006.01) |
| *A61M 21/00* | (2006.01) |
| *F24F 8/50* | (2021.01) |
| *G16H 20/90* | (2018.01) |

(52) U.S. Cl.

CPC .............. *A61B 5/4836* (2013.01); *A61B 5/01* (2013.01); *A61B 5/021* (2013.01); *A61B 5/02405* (2013.01); *A61B 5/0816* (2013.01); *A61B 5/11* (2013.01); *A61B 5/165* (2013.01); *A61B 5/4011* (2013.01); *A61B 5/4803* (2013.01); *A61B 5/4806* (2013.01); *A61M 21/00* (2013.01); *F24F 8/50* (2021.01); *G16H 20/90* (2018.01)

(58) Field of Classification Search

CPC .................. A61M 21/00; A61M 21/02; A61M 2021/0005; A61M 2021/0016; A61M 2021/0083

See application file for complete search history.

(56) References Cited

U.S. PATENT DOCUMENTS

| | | | | |
|---|---|---|---|---|
| 8,385,730 | B2 | 2/2013 | Bushman et al. | |
| 9,446,162 | B2 | 9/2016 | Chandler et al. | |
| 9,675,987 | B2 | 6/2017 | Tillotson et al. | |
| 9,715,242 | B2 | 7/2017 | Pillai et al. | |
| 9,931,425 | B2 | 4/2018 | Edwards et al. | |
| 2010/0023094 | A1 | 1/2010 | Smith et al. | |
| 2017/0319816 | A1* | 11/2017 | Sokol | G04G 5/00 |
| 2017/0340270 | A1* | 11/2017 | Ganesh | A61B 5/4836 |
| 2018/0110960 | A1 | 4/2018 | Youngblood et al. | |
| 2018/0177974 | A1* | 6/2018 | LaPorte | A61M 21/02 |

(Continued)

FOREIGN PATENT DOCUMENTS

| | | | | |
|---|---|---|---|---|
| KR | 102020299 | * | 9/2019 | A61M 21/02 |

*Primary Examiner* — Carrie R Dorna

(57) ABSTRACT

Intelligent aromatherapy using sensor fusion, artificial intelligence, and a dispenser which diffuses a programmable mixture consisting of a precise combination of a plurality of scents optimized to stimulate or alleviate specific physical or mental conditions. Analysis, diagnosis, prescription, and aromatherapy tailoring are implemented by measuring and deducing the physical state of the subject and tailoring the aromatherapy to mitigate problems identified in the detection phase. Continuous biometric feedback can further provide additional information on the subject's response to the aromatherapy and further tailor the therapy to provide the desired effect.

19 Claims, 21 Drawing Sheets

(56) References Cited

U.S. PATENT DOCUMENTS

| | | | |
|---|---|---|---|
| 2018/0357647 | A1 | 12/2018 | Ur |
| 2019/0209806 | A1 | 7/2019 | Allen et al. |
| 2020/0276353 | A1 | 9/2020 | Juving-Brunet |

* cited by examiner

| Name | Scientific Name | Treatment Uses | Strength of Initial Aroma | Volatility |
|---|---|---|---|---|
| Basil | Ocimum basilicum | Exhaustion, Apathetic, Boredom | Medium | Top |
| Bergamot Mint | Mentha citrata / Mentha aquatica L. var. Citrata | Anger, Worried, Tired, Anxiety | Medium, Strong | Top, Middle |
| Cardamom | Elettaria cardamomum | Fatigue, Stress | Medium | Middle |
| Chocolate Peppermint | Mentha piperita v. Chocolat | Exhaustion, Vertigo | Strong | Top |
| Cinnamon | Cinnamomum verum / Cinnamomum zeylanicum | Stress | Strong | Middle |
| Eucalyptus Globulus | Eucalyptus globulus | Melancholy, Uncomfortable | Strong | Top, Middle |
| Eucalyptus Radiata | Eucalyptus radiata | Muscular Aches And Pains, Headaches, Mental Exhaustion, Fatigue, General Simulant and Tonic | Medium | Top, Middle |
| Ginger | Zingiber officinale | Nervous Exhaustion, Apathetic, Uncomfortable | Medium, Strong | MiddleBase |
| Holy Basil | Ocimum sanctum / Ocimum gratissimum / Ociumum tenuiflorum | Headache, Mental and Physical Fatigue, Anxiety | Strong | Top |
| Jasmine | Jasminum grandiflorum | Depression, Exhaustion, Tired, Anxiety | Strong | Middle |
| Lavender | Lavandula angustifolia / Lavandula officinalis | Anxiety, Depression, Stress, Vertigo, Anger, Sad, Worried, Uncomfortable, Tired | Medium | Top, Middle |
| Lemon | Citrus limon | Fragrance, Apathetic | Strong | Top |

Figure 18

| Name | Scientific Name | Treatment Uses | Strength of Initial Aroma | Volatility |
|---|---|---|---|---|
| Marjoram | Origanum majorana | Muscle Relaxant, Stress, Anxiety, Boredom, Worried, Uncomfortable, Tired, Fear | Medium | Middle |
| Melissa | Melissa officinalis | Insomnia, Sleep Disorders, Nervousness, Stress, Anxiety-related Symptoms, Depression | Strong | Top, Middle |
| Neroli | Citrus aurantium | Depression, Insomnia, Shock, Stress | Strong | Middle |
| Nutmeg | Myristica fragrans | Nervousness, Tension, Apathetic | MediumStrong | Middle |
| Peppermint | Mentha piperita | Exhaustion, Vertigo, Apathetic, Uncomfortable, Tired | Strong | Top |
| Roman Chamomile | Anthemis nobilis/ Chamaemelum nobile | Insomnia, Stress, Anger, Worried, Uncomfortable, Tired, Anxiety | MediumStrong | Middle |
| Rosalina | Melaleuca ericifolia | Restlessness, Nervousness, Irritability, Relaxation | MediumStrong | Top |
| Rose | Rosa damascena | Depression, Stress, Anger, Sad, Uncomfortable, Anxiety | Strong | Middle |
| Rosemary | Rosmarinus officinalis | Apathetic, Uncomfortable | MediumStrong | Middle |
| Rosewood | Aniba rosaeodora | Nervousness, Depression, Anxiety, Stress | Medium | Middle |
| Sandalwood | Santalum album | Depression, Stress, Sad, Worried, Tired | Medium | Base |
| Spearmint | Mentha spicata / Mentha cardiaca | Exhaustion | Medium | Top |
| Tangerine | Citrus reticulata | Stress-induced Insomnia, Nervous Exhaustion, Fatigue, Irritability, Sadness, Anxiety | Medium | Top |
| Tea Tree | Melaleuca alternifolia | Fragrance, Anti-Bacteria, Anti fungus, Antiseptic, Anti Inflamation, Uncomfortable | Medium | Middle |
| Ylang Ylang | Cananga odorata var genuina | Anxiety, Depression, Stress, Anger, Worried, Tired | Medium | Base |

Figure 18 ctd.

INTELLIGENT AROMATHERAPY SYSTEM

CROSS-REFERENCE TO RELATED APPLICATION

This application claims priority to United States provisional patent application U.S. 63/121,439 filed 4 Dec. 2020, which is hereby incorporated by reference herein in its entirety.

FIELD OF THE INVENTION

The present invention pertains to an intelligent aromatherapy system, method, and apparatus that takes advantage of biometrics to tailor aromatherapy for a subject. In particular, the present invention provides an intelligent aromatherapy system that is integrated with biometric measurement to understand the emotional and health wellness state of a person and respond accordingly to provide tailored aromatherapy to improve the person's health and emotional state.

BACKGROUND

Humans are primarily auditory and visual animals, and olfaction is a long neglected dimension of modern human experience. Aromatherapy has been around as far back as 2700 BC when Shen Nung's Pen Ts'ao cataloged 365 entries on medicaments and their description. In 60 A.D. Greek physician Pedanios Dioscorides published "De Materia Medica" which was considered the standard textbook for Western medicine for 1,500 years and contained a list of 500 aromatic plants and 4,740 separate medicinal uses for them. The effectiveness of aromatherapy for resolving emotional and health issues is well documented, however current practices haven't evolved significantly and are generally insensitive and depend on qualitative feedback from users rather than quantifiable data.

Emotions are the least understood aspect of modern medical science, and even in the field of psychology little emphasis is placed on the study of emotions and how they affect health. Humans are emotional beings and experience many ups and downs on a regular basis. If these emotions are left unchecked they can create short and long term health and wellness problems. Mental disorders are on the rise in every country in the world and are expected cost the global economy $16 trillion by 2030 (The Lancet Commission on Global Mental Health and Sustainable Development. The Lancet, 2018, Vol. 392, No. 10157). Further, research has revealed that 70% of individuals with mental health issues never seek treatment (C. Henderson et al., Am. J. Public Health 103(5); May 2013) and poor mental health can evolve into serious and potentially chronic and life-shortening medical conditions if left untreated. The Lancet Commission on Global Mental Health (2018) recommends that mental health should be reframed as a fundamental human right. Rising healthcare costs is fuelling a growing need for alternate wellness options for prevention and ailment mitigation and for promoting proactive healthy lifestyle management.

Various methods are used to control the scent in a room to provide a sense of wellbeing to the people within. In one example described in U.S. Pat. No. 9,715,242 to Pillai et al., a scent subsystem is operable to selectively dispense one or more scents into the air of a room. The scent subsystem may have one or more reservoirs which hold various scents and a control subsystem can selectively introduce scents into the air in the room from the reservoirs according to a schedule.

In another example, United States patent application US20180357647 to Ur describes A computer implemented method, a computerized system and a computer program product for selective scent dispensing where a scent can be personalized to a person based upon characterization of the person.

In another example, U.S. Pat. No. 9,675,987 to Tillotson et al. describes clothing having a device for measuring a biometric property and determining when the biometric property is within a predetermined range, above a predetermined level or below a predetermined level, and a dispenser for dispensing a fluid into an area surrounding the device when the one or more biometric properties is determined by the processing stage to be within the predetermined range, above the predetermined level or below the predetermined level.

Current aromatherapy devices are completely unaware of the state of a subject. They are passive, unresponsive, and release a single fixed fragrance at any given time which doesn't account for variations in the subject's state of health or psychological state. There remains a need for an intelligent aromatherapy system that is integrated with biometric sensor fusion measurement to understand the emotional and health state of a person and respond accordingly to provide tailored aromatherapy to improve the person's health and emotional state.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an intelligent aromatherapy system that is integrated with biometric sensor fusion measurement to provide tailored aromatherapy to improve the person's health and emotional state. Another object of the present invention is to understand the emotional and health state of a person using aromatherapy and biometric sensor fusion measurement to diagnose a person's health and emotional state.

In an aspect there is provided a method of providing aromatherapy comprising: measuring a biometric condition of a subject; evaluating the biometric condition to establish a state of the subject in their environment; prescribing an aromatherapy prescription based on the state of the subject using a prescribing algorithm, the aromatherapy prescription comprising a recipe of scents to treat the state of the subject; delivering the aromatherapy prescription to the subject by a diffuser; remeasuring the biometric condition of the user; and adjusting the aromatherapy prescription to change the biometric condition.

In another aspect there is provided a method of providing aromatherapy comprising: measuring biometric data on a subject using a plurality of biometric sensors, each of the plurality of biometric sensors obtaining a measurement of a biometric condition over time; transmitting the biometric data to a processor and evaluating the biometric data to establish a physiological state of the subject; prescribing an aromatherapy prescription based on the physiological state of the subject, the aromatherapy prescription comprising a recipe of scents and treatment conditions to treat the physiological state of the subject; delivering the aromatherapy prescription to the subject; remeasuring the biometric data of the subject; and adjusting the aromatherapy prescription to tailor the aromatherapy prescription and change the biometric condition in the subject. In an embodiment, the biometric condition is heart rate, ECG, blood oxygen, body temperature, breathing rate, heart rate variability, body movement, sleep state, facial expression, subject sounds, speech patterns, eyelid state, and blood pressure, or a combination thereof.

In another embodiment, the aromatherapy prescription comprises the regularity, intensity, and duration of treatment.

In another embodiment the method further comprises measuring an environmental condition and incorporating the environmental condition into the prescribing algorithm to tailor the aromatherapy prescription to the subject.

In another embodiment the environmental condition is indoor temperature, room size, room humidity, outdoor temperature, outdoor humidity, atmospheric pressure, altitude, airborne contaminant concentration, or a combination thereof.

In another embodiment the method further comprises incorporating personal data of the subject into the prescribing algorithm, the personal data comprising gender, sex, age, mass, allergies, or a combination thereof.

In another embodiment the method further comprises sensing a distance of the subject to the diffuser and changing the amount of diffused aromatherapy accordingly.

In another embodiment the method further comprises varying the aromatherapy prescription over time to avoid subject olfactory blindness.

In another embodiment the method further comprises raising a vital sign alarm when the biometric condition indicates a concerning state.

In another embodiment the prescribing algorithm uses prior subject data, big data collected from multiple subjects, artificial intelligence, or a combination thereof.

In another embodiment the method further comprises analysing the biometric condition using machine learning to improve the prescribing algorithm.

In another embodiment the method further comprises transferring the aromatherapy prescription to a scent patch.

In another aspect there is provided an aromatherapy diffuser apparatus comprising: a plurality of reservoirs for storing a plurality of scents; a plurality of dedicated actuators, each actuator connected to one of the plurality of reservoirs; a microcontroller for controlling each of the dedicated actuators to control an aromatherapy recipe and amount of scent to be ejected from each of the plurality of reservoirs; and a control board for receiving remote commands to adjust the aromatherapy recipe and connected to the microcontroller to control dispense of the aromatherapy recipe.

In an embodiment, the apparatus uses thermally controlled low temperature diffusion to diffuse the aromatherapy.

In another embodiment, the plurality of reservoirs are housed in a cartridge.

In another embodiment the apparatus further comprises a display to indicate the status of the reservoirs in the cartridge In another embodiment the apparatus further comprises one or more environmental sensor.

In another embodiment the environment sensor is a camera, thermal camera, ultrasonic sensor, sound sensor, or combination thereof.

In another embodiment the apparatus further comprises one or more biometric sensor.

In another embodiment the biometric sensor is a camera or an infrared camera.

In another embodiment the aromatherapy recipe comprises a dynamic sequencing of scents over time.

In another embodiment the apparatus further comprising a memory storage device for storing a plurality of aromatherapy recipes for controlling the microcontroller, and a processor for adjusting the aromatherapy recipe based on biometric data.

In another aspect there is provided a system for providing aromatherapy comprising: a biometric sensor for measuring biometric data of a subject over time on one or more biometric conditions of a subject; an aromatherapy diffuser comprising: a plurality of scent reservoirs, each scent reservoir comprising an aromatherapy scent; and an electronic control board for controlling a plurality of actuators, each actuator connected to one of the scent reservoirs; and a processor for receiving biometric data from the biometric sensor pertaining to the biometric condition of the subject and prescribing an aromatherapy prescription based on the assessed biometric condition of the subject, the processor connected to the electronic control board in the aromatherapy diffuser to provide instructions to the aromatherapy diffuser to deliver an aromatherapy prescription comprising scents from the scent reservoirs according to a treatment condition for changing one or more of the biometric conditions of the subject.

In another aspect there is provided a system for providing aromatherapy comprising: a biometric sensor for measuring a biometric condition of a subject; an aromatherapy diffuser comprising: a plurality of scent reservoirs, each scent reservoir comprising an aromatherapy scent; and an electronic control board for controlling output of each of the scent reservoirs and connected to the biometric sensor, the electronic control board capable of receiving and sending wireless signals; an aromatherapy assessment engine for receiving data from the electronic control board pertaining to the biometric condition of the subject and assessing the state of the subject; and a prescription engine for prescribing an aromatherapy recipe based on the assessed state of the subject and connected to the electronic control board in the aromatherapy diffuser such that the aromatherapy diffuser can deliver the aromatherapy recipe comprising scents from the scent reservoirs.

In an embodiment the system further comprises an environmental sensor for measuring an environmental condition near the aromatherapy diffuser.

In another embodiment the assessment engine is further connected with the internet and wherein the assessment engine further incorporates environmental data in assessing the state of the subject.

In another embodiment the environmental data comprises one or more of weather data, location data, outdoor temperature, outdoor humidity, atmospheric pressure, precipitation, altitude, and pollution levels.

In another embodiment the system further comprises a vital sign alarm to provide an alert when the biometric condition indicates a concerning state.

In another embodiment the aromatherapy prescription is delivered based on a permutation, interval, and precision process that is specific to the physiological state of the patient, where permutation provides information on what scent or combination of scents to deliver based on the availability in the essential oil reservoirs, precision is a determination of how much of a particular essential oil or scent or combination of scents to diffuse at a particular time or over a time period, and interval is a determination of how long a particular therapy should be given without producing olfactory blindness.

BRIEF DESCRIPTION OF THE FIGURES

For a better understanding of the present invention, as well as other aspects and further features thereof, reference is made to the following description which is to be used in conjunction with the accompanying drawings, where:

FIG. 18 is a table providing a non-limiting list of example aromatherapy scents that may be used with the present system and method.

DETAILED DESCRIPTION OF THE INVENTION

Figure 1:
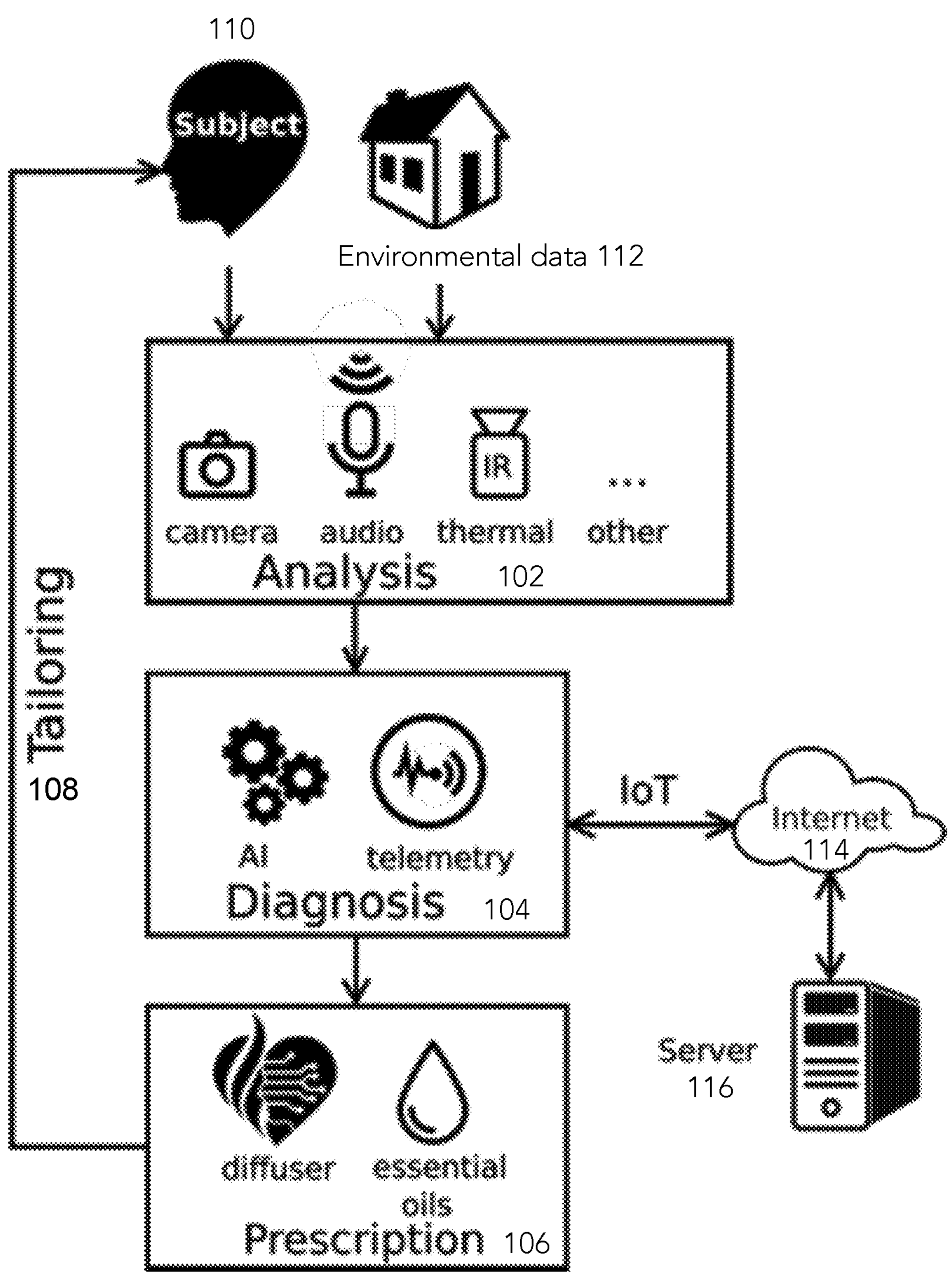
FIG. 1 is a flowchart of an embodiment of the system.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprise" and any of its derivatives (e.g. comprises, comprising) as used in this specification is to be taken to be inclusive of features to which it refers, and is not meant to exclude the presence of any additional features unless otherwise stated or implied. The term "comprising" as used herein will also be understood to mean that the list following is non-exhaustive and may or may not include any other additional suitable items, for example one or more further feature(s), component(s) and/or element(s) as appropriate. The terms "comprising," "having," "including" and "containing," and grammatical variations thereof, are inclusive or open-ended and do not exclude additional, unrecited elements and/or method steps. The term "consisting essentially of" when used herein in connection with a composition, device, article, system, use, or method, denotes that additional elements and/or method steps may be present, but that these additions do not materially affect the manner in which the recited composition, device, article, system, method, or use functions. A composition, device, article, system, use, or method described herein as comprising certain elements and/or steps may also, in certain embodiments consist essentially of those elements and/or steps, and in other embodiments consist of those elements and/or steps, whether or not these embodiments are specifically referred to.

As used herein, the term "about" refers to an approximately +/−10% variation from a given value. It is to be understood that such a variation is always included in any given value provided herein, whether or not it is specifically referred to. The recitation of ranges herein is intended to convey both the ranges and individual values falling within the ranges, to the same place value as the numerals used to denote the range, unless otherwise indicated herein.

The use of any examples or exemplary language, e.g. "such as", "exemplary embodiment", "illustrative embodiment" and "for example" is intended to illustrate or denote aspects, embodiments, variations, elements or features relating to the invention and not intended to limit the scope of the invention.

As used herein, the terms "connect" and "connected" refer to any direct or indirect physical association between elements or features of the present disclosure. Accordingly, these terms may be understood to denote elements or features that are partly or completely contained within one another, attached, coupled, disposed on, joined together, in communication with, operatively associated with, etc., even if there are other elements or features intervening between the elements or features described as being connected.

As used herein, the term "aromatherapy" refers to the use of scents to cause a physiological response. The term "aromachology," which refers to the study of why and how certain scents trigger a psychological or physiological response, is closely related to aromatherapy. Although the term "aromatherapy" is used herein, it is understood that the presently described system, method, and device can also be used in aromachology.

As used herein, the term "scent" refers to any airborne compound, mixture or chemicals, or molecule that can be inhaled by a person or animal. Most chemical compounds that are classified as scents are detectable by the human nose as having a smell, however it is understood that some airborne molecules that are not detectable to a person may also be used in the present invention and have therapeutic benefit. Sources of scent as used in the presently described aromatherapy system, method, and apparatus can include but are not limited to essential oils, pure plant extracts that contain one or more aromatic or chemical component, and purified extracts that contain only a single component. Although naturally occurring extracts from plants are preferred for human health reasons, it is also conceivable that synthetic scents could also be used. The term "scent" can refer to a single chemical, and also to a combination of chemicals or mixture of chemicals.

As used herein, the term "biometric" refers to a measurement that can be taken of a subject's physiological, emotional, psychological, biological, chemical, or physical state. Biometric measurements include but are not limited to vital signs such as heart rate, ECG, blood oxygen, body temperature, breathing rate, heart rate variability, body movement, sleep state, facial expression, subject sounds, speech patterns, eyelid state, and blood pressure. A biometric sensor is an electronic sensor capable of measuring a biometric state of a subject.

Herein is described an intelligent aromatherapy system, method, and apparatus that takes advantage of biometric sensor fusion measurements to tailor aromatherapy for a subject. Intelligent aromatherapy as presently described includes biometric sensor fusion measurements and aromatherapy which when analysed together provide tailored aromatherapy can improve a person's health and emotional state. The presently described intelligent aromatherapy system is integrated with multi-modal biometric measurements of biometric conditions which are physiological measurements such as vital signs, voice, facial expressions, physical activity, sleep, etc., which are combined by sensor fusion to establish a quantitative model of the physiological state of the subject. The physiological state of the subject is also carefully intertwined with the psychological state and mental health state, and both can be effectively treated using the present system and method. The biometric condition data can further be incorporated with environmental measurements such as external weather, room temperature, etc. to enable a quantifiable understanding the emotional and health wellness state of a person and respond accordingly to provide tailored aromatherapy to improve the person's health, wellness, and emotional state by changing the biometric condition. Through the combination of aromatherapy and biometric measurement the present system and method collects a person's response to aromatherapy by biometric measurement and uses the collected biometric data to understand the emotional and health state of a person using aromatherapy. Biometric sensor fusion measurement over time in response to aromatherapy can also assist in diagnosing a person's health state and emotional state. Sensor fusion is the combining of sensory data or data derived from disparate sources such that the resulting information has less uncertainty than would be possible when these sources were used individually.

Incorporating biometric measurement and aromatherapy in the way described provides a scientifically obtained personalized aromatherapy prescription to tailor the aromatherapy specifically for the subject. The present system can yield early detection of negative emotional and health patterns, compute a prognosis, and can take intelligent preventive action to slow, stop or reverse the progression of a disorder or negative or deleterious physiological state. A preventative approach through early detection by sensor fusion and artificial intelligence can also provide the subject with a customized aromatherapy to mitigate any issues before they develop into a serious condition or state.

The present system can thus provide a customized prescription to mitigate mental health problems and provide warnings of any deterioration in patient condition. The present system can also provide an interface to the subject's vital signs, which offers a welcome complement or replacement for standard medical sensors used in typical clinical scenarios and increases patient comfort and mobility. The present system can also include a vital sign alarm to warn a healthcare worker, caregiver, or contact system of patients in distress, particularly mental health distress, potentially saving lives. A vital sign alarm or alert can be triggered when a biometric condition indicates a concerning state, such as one that rapidly rises, drops, or is outside of a normal range. In addition, a vital sign alarm can be triggered when the overall state of the subject is deemed to be concerning by biometric sensor fusion, such as one indicative of a rapid change in or overall tendency for a concerning physical, emotional, physiological, or psychological state.

The present fully automated aromatherapy approach utilizes a multi-model system which combines the predictions from multiple inputs of, for example, vital signs, voice emotions and facial expression, as well as social state and environmental measurements, and weights the predictions to predict a final emotional or physiological state. Sensor fusion from the multiple biometric sensor data inputs combines data from various sensors such as biometric sensors, camera, microphone, environmental sensors, etc., to accurately determine a person's emotion and physical state. Scientifically tailored aromatherapy can then be delivered based on a permutation, interval, and precision (PIP) process that is specific to the psychological state of the patient, where permutation provides information on what scent or combination of scents to deliver based on the availability of the essential oil reservoirs, precision is a determination of how much of a particular essential oil or scent or combination of scents to diffuse at a particular time or over a time period, and interval is a determination of how long a particular therapy should be given without producing olfactory blindness. A determination of the regularity, intensity, and duration (RID) of the multi-model system also enables enhanced situational awareness and responsiveness, where regularity answers the question "how frequent is the emotion experienced?", intensity answers the question "how intense is the experienced emotion?", and duration answers the question "how long has user been experiencing the emotion?". Sensor fusion patterns of biometric data have been found to be correlated to specific emotions in specific individuals, and that treatment using aromatherapy to change the biometric condition of an individual can alleviate or change the emotion. The RID and PIP models are used in the present intelligent aromatherapy method and system to correlate historical data of detected emotions and prescriptions to better understand a person's emotion patterns, predict/detect early warnings of emotion abnormalities, and provide tailored therapy to prevent the progression of the condition. The aromatherapy diffusion is thereby orchestrated to improve olfactory receptor activation for continuous benefit and comfort without producing olfactory blindness.

Current research on the health benefits of aromatherapy for various conditions and psychological states are often performed qualitatively and non-scientifically and the results are frequently inaccurate and generic, meaning that prescription apply to everyone instead of to a specific person. In the present system, intelligent aromatherapy uses sensor fusion, artificial intelligence, and an aromatherapy dispenser or diffuser apparatus which dispenses a programmable mixture of airborne scent. In one application, an aromatherapy dispenser apparatus can be used that has a plurality of scent reservoirs capable of providing a precise combination or recipe of scents optimized to stimulate or alleviate one or more specific physical or mental conditions by changing one or more biometric conditions in a subject. Intelligent aromatherapy personalizes this research quantitatively, scientifically and automatically using sensors and artificial intelligence to provide an effective therapy targeted to address the needs of a specific individual and their particular health issue in real-time. By blending multiple essential oils into a prescription, multiple physical and mental conditions may also be alleviated simultaneously.

By personalizing aromatherapy in real-time using biometric sensor data, artificial intelligence and using a plurality of essential oil components or scents, a wide spectrum of prescriptions can designed and prescribed to stimulate or alleviate specific physical or mental conditions for an individual person. This can be achieved by measuring a plurality of biometric conditions to determine the physiological state of a subject and correlating the collected data using sensor fusion and machine learning to provide a diagnosis which is used to engineer an appropriately customized olfactory environment which improves or maintains the subject's state. This process referred to herein as intelligent aromatherapy, provides a scientifically based, automatic, and quantitative approach to aromatherapy personalization. Therapy can be dispensed on-demand as per subject request or condition, and can be automatically dispensed based on the subject's physiological state. Therapy can also be tailored as the subject's physiological state as measured by data collected on the subject's biometric conditions improves or deteriorates. Data is continuously collected on the subject's bio-signal, environment, and social state throughout the therapy to track how the subject responds to the therapy and provide tailored therapy to the individual subject.

Globally more than 70% of people with mental illness receive no treatment from health care staff." (C. Henderson et al., Am. J. Public Health 103(5); May 2013). This problem originates from four contributing factors (1) lack of knowledge to identify features of mental illness, (2) ignorance of how to access treatment, (3) prejudice against people who have mental illness, (4) expectation of discrimination against people diagnosed with mental illness. The present intelligent aromatherapy system effectively addresses all of these factors by (1) identifying early features of mental illness or by predicting the development of mental illness, (2) automatically providing therapy to slow, stop or reverse the progression of mental illness, (3, 4) the therapy is completely private, alleviating fears of prejudice or discrimination.

FIG. 1 is a flowchart of an embodiment of the system including four tightly coupled phases of intelligent aromatherapy: an analysis phase 102; a diagnosis phase 104; a prescription phase 106; and a tailoring phase 108. Existing smart aromatherapy devices merely react to subject states such as subject-reported wellness, however the present system can predict what may happen based on biometric measurement and higher level subject biometric condition states and intentions and takes a proactive approach to prevention. The system can also further leverage big data techniques to share continual improvements to prescriptions obtained during the tailoring phase with the rest of the community to further improve aromatherapy treatment for all subjects.

The hardware and software architecture of the present system can be grouped under two general steps of detection, which includes analysis and diagnosis, and therapy, which includes prescription and tailoring. The analysis and diagnosis phases 102, 104 implement detection by measuring and deducing the state of the subject using biometric measurements obtained from biometric sensors, and optionally environmental measurements around the aromatherapy apparatus, inside and/or outside. The prescription and tailoring phases 106, 108 implement aromatherapy by taking action to provide a prescription which attempts to mitigate issues revealed in the detection phases.

In the detection step, the first phase is the analysis phase 102, in which the state of the subject and their environment is measured using sensors either on the aromatherapy delivery apparatus, from remote biometric sensors, or both. Various biometric sensors can be used, such as, for example, on wearable devices, smart sensors, cameras, thermal imagers, and smart watches. Remote sensing devices can also be used for detection of environmental data 112 factors around the aromatherapy apparatus, which include but are not limited to one or more camera, thermometer, barometer, hygrometer, photo-sensor, UV sensor, and microphone. The biometric sensors can receive data such as audio, image, and thermal images to measure the state of the subject 110, as well as ultrasonic sensors to measure environmental data 112 parameters such as the size of the room, distance to the subject etc. In the second phase of the detection step a diagnosis is made. Through indoor environment sensors, the present system can calculate the exact amounts essential oils to prescribe for the given room dimensions to provide the optimum atmospheric concentration to mitigate problems. Environmental conditions can include in indoor environment such as the room size, subject distance from diffuser, indoor temperature, indoor humidity, and presence of airborne chemicals, contaminants, or particulate. The environmental data 112 or outdoor weather conditions can also be considered, as weather and temperature are known to have a significant effect on the physical and mental health of many people. Weather and external environmental data 112 can be taken from an internet 114 reporting of local weather based on location, including temperature, humidity, atmospheric pressure, precipitation, altitude, and pollution levels. Sensor fusion from various biometric readings over time, telemetry, and artificial intelligence, can provide a diagnosis of the subject 110 physiological state via an analysis of each measured biometric condition, which can be inferred in real-time, including the subject's physiological health status, mental state, and emotional state. Historical data and/or previously obtained baseline biometric data on the subject 110 can also be used as comparison, as well as big data from other subjects and trend detection from the subject data and data of other subjects.

In the second step of therapy, an aromatherapy prescription can be determined based on the diagnosis, and a custom aromatherapy recipe is designed to stimulate or alleviate specific physical or mental conditions of the subject. The prescription and tailoring phases 106, 108 implement the therapy by taking an action which mitigates problems discovered in the detection phases by creating a mixture of essential oils or scents specifically designed to improve or maintain the subject state in real-time. The prescription phase creates the mixture of essential oils specified by the diagnosis phase then diffuses it into the atmosphere. The tailoring phase 108 closely monitors the subject's reaction to the prescription and tailors the prescription to optimize the subject's response and change the desired biometric condition. The tailoring phase 108 can also make predictions on the future state of the subject 110 by performing an ongoing analysis of subject history. In the final tailoring phase 108, the subject's response to the therapy is analyzed through the biometric sensors and the prescription is dynamically tailored in real-time to optimize the subject state through treatment, and to potentially make predictions about their future state based on the response to therapy. The optimum aromatherapy for the subject's condition can also be transferred to a patch for mobile applications. The aromatherapy can be delivered in any suitable method, such as by a diffuser. Alternatively, personal delivery devices can also be used that deliver the aromatherapy prescription more directly to a person's nose, such as using an inhaler device such as a nebulizer through which the therapy is delivered. Accompanying colour and sound therapies can also be provided along with the aromatherapy.

The present system provides a quantitative, data-based, scientific, full spectrum approach to detect subject emotions, provide a diagnosis of subject state, and mitigates any wellness roadblocks through intelligent aromatherapy. The present system thus actively participates in the pro-active management of subject health and wellness by taking appropriate action based on subject current and predicted future state based on current biometric data and individual biometric data patterns over time. The analysis, diagnosis, prescription, and tailoring cycle can deliver an optimal aromatherapy for a particular period of time, however it is clear that the physiological and environmental state of the subject can change, which may necessitate a change in the prescribed remedy to adjust to the change. The present system and method can respond to the change by adjusting the aromatherapy recipe remedy. In this way, intelligent aromatherapy can automatically personalize the prescription and remedy based on real-time measurements of the current state of the subject and synthesize a large variety of prescriptions using a programmable mixture of multiple scents or essential oils to diffuse the exact dose and recipe to optimally alleviate a specific condition in a specific subject with high precision.

In addition, the present system can compare biometric data with a database of biometric data from a single subject over time and from multiple subjects to predict healing aromatherapy treatments and also potentially diagnose symptomatic changes. The present system also provides fully personalized prescriptions to continuously improve based on automated sensor fusion feedback and artificial intelligence to adapt to all scenarios. By leveraging intelligent automated feedback, the present system is capable of tracking the state of the subject over a period of time and learns to provide more effective therapies by optimizing the aromatherapy recipe including the relative volume of each essential oil component in the prescription mixture as well as adjusting the overall dose.

The present system is also aware of the subject data and incorporate subject preconditions to the measured biometric state. For example, the system can release a lower dose for example if the subject is female, as females generally have a heightened sense of smell compared to males. Pregnancy can also be detected as the sense of smell and sensitivity to smell changes during pregnancy. In addition, some essential oils are contra-indicated for subjects with various preconditions such as epilepsy or for pregnant women. Current aromatherapy practices are insensitive to these conditions and may diffuse potentially harmful substances. In contrast, intelligent aromatherapy can detect some of these preconditions or incorporate subject health information into the prescription algorithm for personalization of aromatherapy to the subject and prevent the diffusion of potentially harmful essential oils or scents. In addition, the present system can automatically detect allergic reactions to diffused essential oils via biometric sensors and artificial intelligence by monitoring and detecting changes in biometric conditions, halt the scent diffusion, and provide a safer alternate therapy. The system can also halt or lower the diffusion of a prescription if the subject is located too close to the diffuser to prevent overwhelming them with high concentrations of scent. By detecting the absence of humans in the environment, the system can also halt the therapy thus conserving essential oils and saving money. Most current aromatherapy devices are insensitive to their environment and continue to release essential oils until they are turned off or run out of oils. Uncontrolled release of essential oils wastes money and can lead to detrimental side-effects such as dizziness and nausea.

A customized prescription that changes over time can also mitigate olfactory blindness, also called anosmia or smell blindness, which is the loss of the ability to detect one or more smells, sometimes caused by long term exposure. By carefully orchestrating periodic variations in the relative weights of the multiple essential oils alternate mixtures can be permuted with equivalent effects to prevent olfactory blindness or to provide the subject with a choice of which prescription they prefer.

The computer and server 116 typically include a variety of computer readable media on at a number of locations and in a variety of media. Such media can be any available media that is accessible by the computer and includes both volatile and non-volatile media, removable and non-removable media. The system memory can include computer readable media in the form of volatile memory, such as random access memory (RAM), and/or non-volatile memory, such as read only memory (ROM), as well as remote memory and cloud storage. The system memory typically contains data such as data and/or program modules such as operating system and application software that are immediately accessible to and/or are presently operated on by the processing unit. The computer or server may also include other removable/non-removable, volatile/non-volatile computer storage media. A mass storage device or cloud computing storage can provide a non-volatile storage of computer code, computer readable instructions, data structures, program modules, analytical data, sensor data, and other data for the computer. Mass storage device can include one or more hard disk, removable magnetic disk, removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like. Any number of program modules can be stored on the mass storage device, including by way of example, an operating system and application software. Each of the operating system and application software (or some combination thereof) may include elements of the programming and the application software. Data can also be stored on the mass storage device, and in any form or database known in the art.

Figure 2:
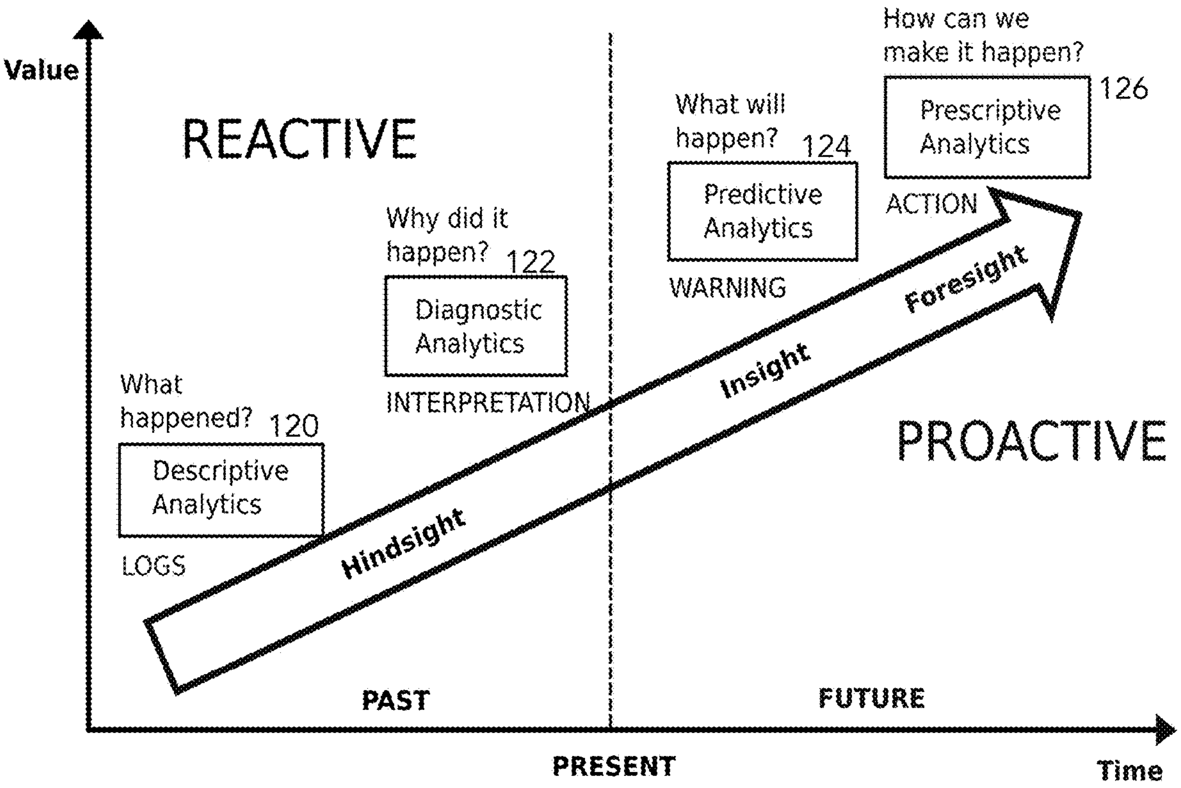
FIG. 2 illustrates an approach of the present system to data analytics.

FIG. 2 illustrates a methodology that shows various approaches to data analytics as utilized in the present system, shown on a value versus time graph. Data analytics can be divided into two general categories, reactive and proactive. Reactive analytics provides hindsight or 'post-mortem' analysis and includes descriptive analytics 120 which logs sensor inputs and reveals what happened, and diagnostic analytics 122 which reveals the deeper causal nature of events and answers the question "Why did it Happen?". Proactive analytics provides insight and foresight, where predictive analytics 124 leverages historical data to come up with predictions and answers the question "What will happen?", and prescriptive analytics 126 takes action based on predictions and answers the question "How can we make it happen?" Although the present system uses all four types of analytics, a strong emphasis is placed on prescriptive analytics, the most valuable type of analytic and the only analytic which takes preventative action.

Figure 3:
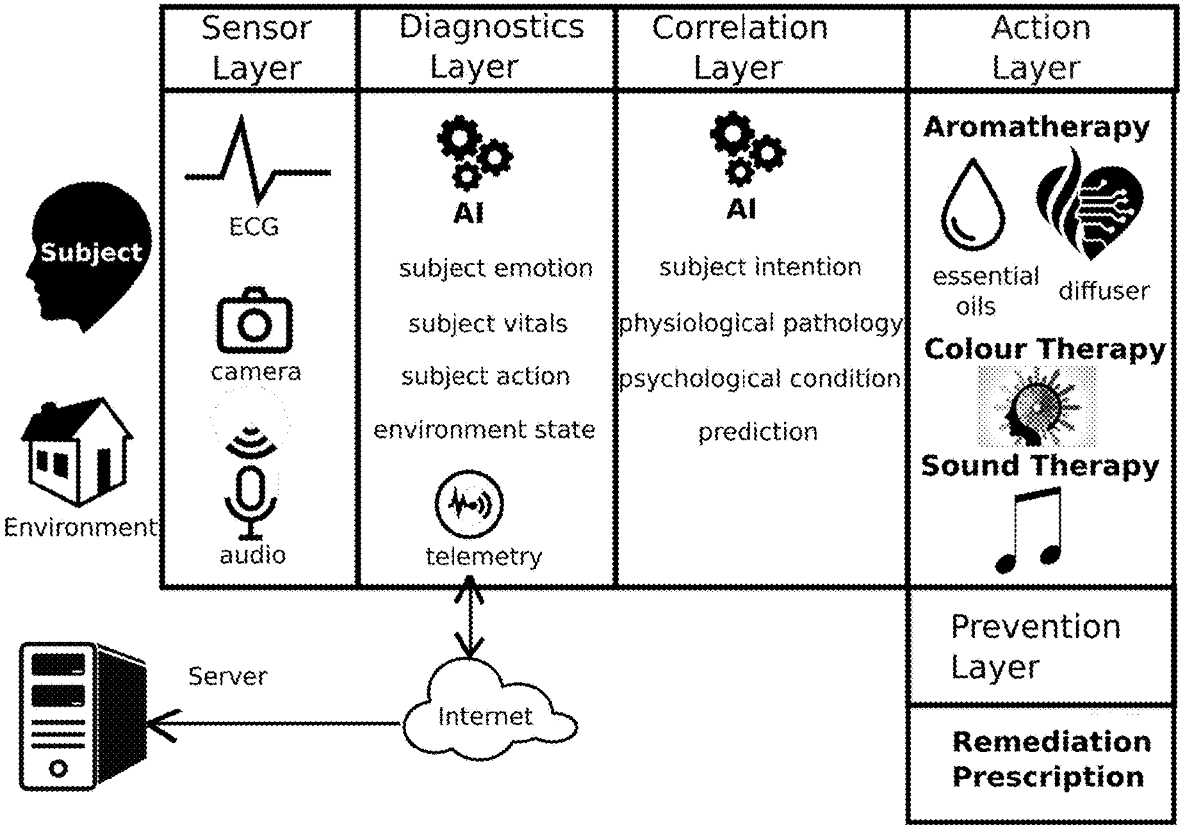
FIG. 3 illustrates the analytics layer architecture of the present system.

FIG. 3 illustrates the analytics layer architecture of the present system. The system architecture has multiple phases such as analysis, diagnosis, prescription and tailoring. This architecture can also be analyzed into the multiple layers which correspond to different types of analytics as shown in FIG. 2. The analysis phase has a sensor layer, and the diagnosis phase has multiple successive layers each of which contribute higher level subject states. For example, starting with low level subject states or biometric conditions or subject vitals such as electrocardiogram (ECG) results from the analysis phase which can be measured using one or more biometric sensor, the diagnostics layer can determine higher level subject states such as emotion, wellness state, subject action etc. Based on these higher level subject states, the correlation layer can then deduce increasingly higher level subject states such as subject intentions, physiological pathology, and psychological abnormalities by synthesizing all lower level subject states into a final prognosis. The correlation layer can also make predictions about subject future state, diagnosis, and treatment. The final two layers, the action layer and the prevention layer, implement the prescription and tailoring phases respectively.

This layered approach to intelligent aromatherapy is implemented using a multiple layer deep learning neural model. Data modeling is based on features, individual measured properties, or characteristics of a phenomena being observed. Deep learning automatically discovers new features when trained on massive amounts of data and supports the auto-discovery of new features because of the closed-loop nature of the feedback provided by the tailoring phase and crowd-sourcing of prescription improvement. Auto-discovered features provide more insight into modeling the domain than hand-crafted ones, resulting in higher accuracy with less computation required, which is important when considering that part of the neural network evaluation process must occur on simple devices with limited resources.

Figure 4:
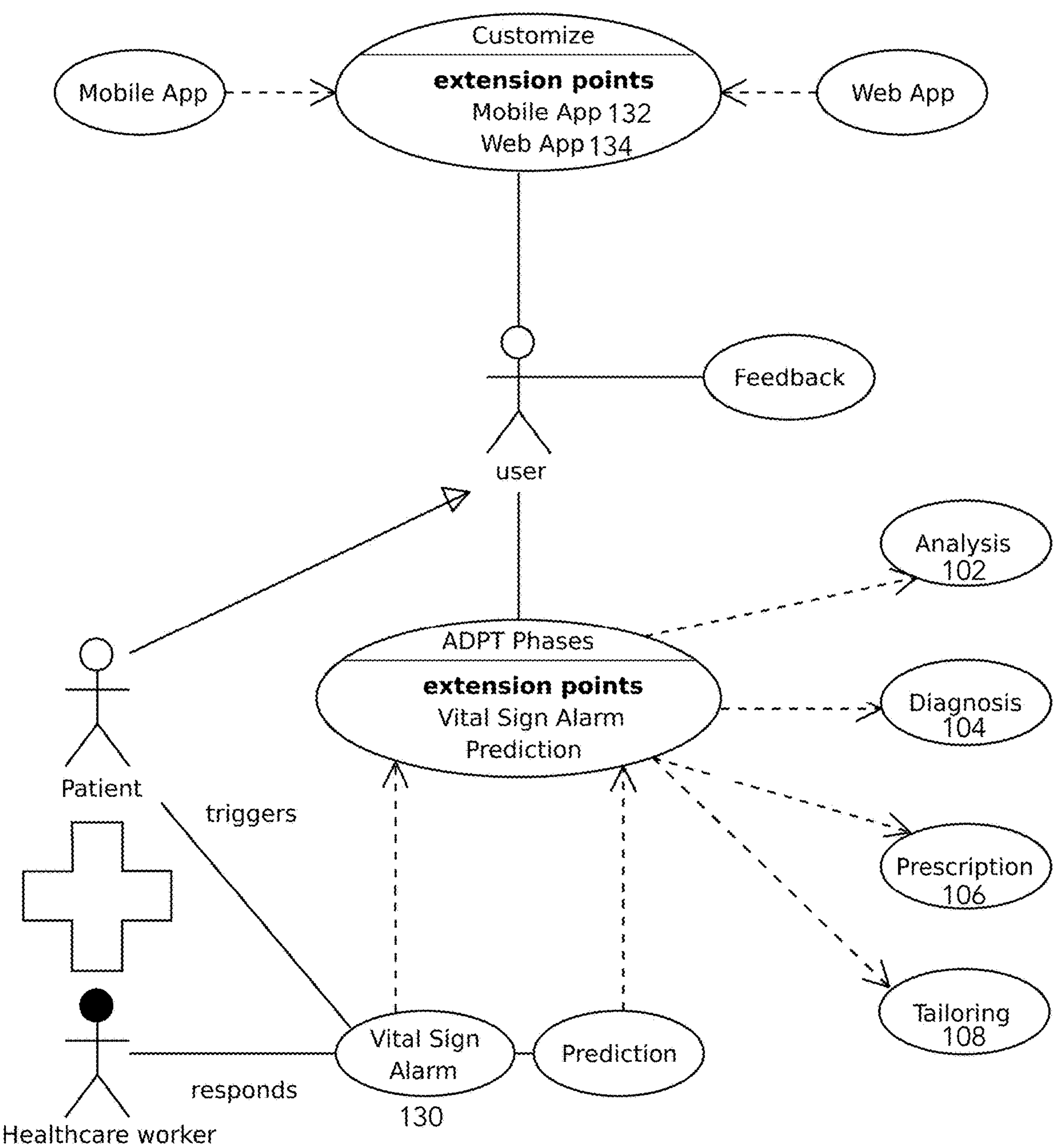
FIG. 4 is a use case diagram illustrating types of users and their interaction with the system.

FIG. 4 is a use case diagram illustrating types of users and their interaction with the system including various use-cases such as analysis phase 102, diagnosis phase 104, prescription phase 106 and tailoring phase 108, also referred to as the ADPT (analysis, diagnosis, prescription, tailoring) phases. Customization can also be achieved by implementing mobile app 132 or web app 134 use cases. Subject information can be entered such as name and other attributes and any pre-conditions or preferences. Although the system can be fully automatic, the subject or patient has the option to choose to be informed on their current state, current prescription and predicted future state via these apps, either continuously or through various levels of notifications or warnings. The app can also provide a facility to manually enter which part of the body or which biometric condition is causing issues, according to the subject, to assist with the automated inference and monitoring of a subject biometric condition. Of particular interest to the medical community is the vital sign alarm 130 which can warn healthcare workers of patients in distress, where distress can be identified by changes to one or more biometric condition as a threshold or in a biometric sensor fusion pattern. Prediction is an extension use case which supports the diffusion of preventive prescriptions and can also have an alarm for warning of future vital sign deterioration. The present system can thereby predict or diagnose a subject state based on biometric readings and provide a response with aromatherapy.

In an example, insomnia can be detected by, for example, a combination increased subject movement and a change in breathing rhythm over time. Other signals can contribute to the diagnosis, including other vital signs and environmental signals such as local sound detection and light detection. The system then hypothesizes that the subject may be having trouble sleeping, or have a sleep disorder, and can prescribe an aromatherapy sleep prescription. Decrease in disturbance during sleep as measured by the biometric condition of the subject can provide an indication that the aromatherapy prescription has treated the sleep disorder, providing additional evidence of a subject's responsiveness to the aromatherapy and correlation to other subjects who have reacted positively to the same treatment. In another example, if a fever is detected the system can diagnose that the subject has an infection and prescribe an aromatherapy remedy, calm the person, or treat the infection. In another example an increase in heart rate can diagnose fear or anxiety, and an anti-fear or anti-anxiety prescription can be released. In yet another example if an odd behaviour detected, such as that carried out by people with Obsessive Compulsive Disorder (OCD), a mitigating OCD therapy can be released. In another example, the system can detect, using biometric condition data, that a subject experiences abnormal stress levels at a particular time of day based on the biometric pattern of data collected. At the high stress time of day the system can anticipate the subject stress condition and symptoms and try to proactively relieve the stress response by delivering an appropriate aromatherapy. On-demand treatment can also be made available by the system to a subject if the person is feeling stressed, ill, or has an self-identifiable condition or symptom that they would like to treat. The subject can then request a treatment of the system by symptom or condition name. The system can then locate a therapy that will address the subject condition and provide it to the subject. If no therapy prescription is available for the condition or symptom identified by the subject then the system can advise the person and optionally identify a different treatment that may be of interest to the subject.

Figure 5:
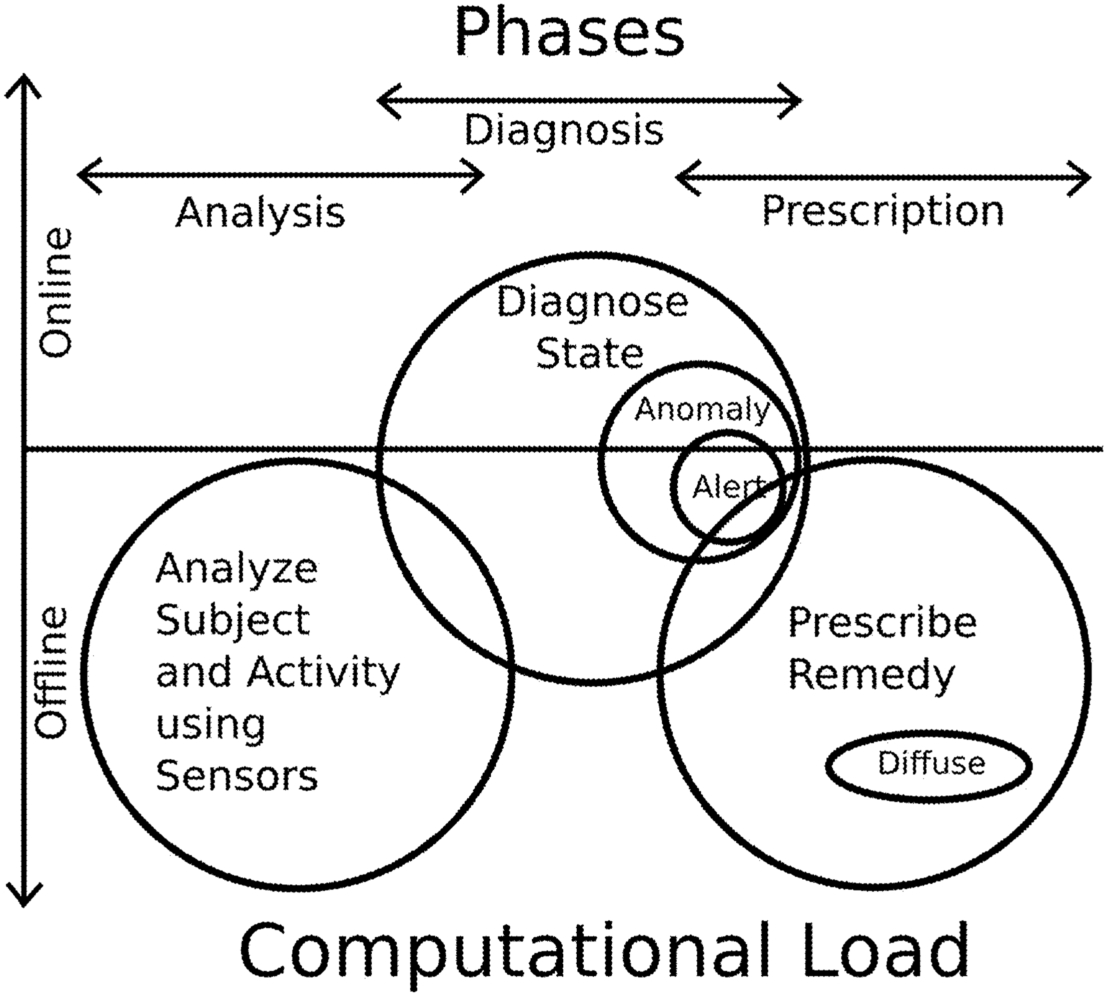
FIG. 5 illustrates the distribution of computational load between local and remote computing resources.

FIG. 5 illustrates the distribution of computational load between local and remote computing resources. In the detection of subject and activity, for example, audio domain microphone sensors can be used to determine the absolute loudness of environmental noise which can induce stress if it exceeds a certain decibel level. Speech can be recognized into text and sentiment analysis can further be performed to reveal subject psychological state. Voice recognition in a natural language user interface can also be used, and inflections in the subject's voice patterns can reveal their emotional state. With the assistance of artificial intelligence audio sensors can also be used to detect and determine music genres which contribute in the determination of a subject's psychological state. When an atmospheric diffuser is used, an ultrasonic detector can be used to ensure that the subject is located beyond a minimum distance from the device before the diffuser releases a prescription. This allows the mixture to diffuse in the air and reach its optimal concentration. In the optical domain a video camera can be used to interpret the actions performed by a subject in order to determine both their physiological and psychological state. The relative dimensions of the subject image on a video sensor can also provide a crude estimate of the distance to the subject which can assist the ultrasonic range finder in determining subject range. The interpretation of facial expressions as picked up by a camera can also reveal specific emotions. Physiological vital signs can be measured with specific biometric sensors, but also by using a camera. For example, heart rate can also be measured by the frequency of oscillations in the change in skin color, breathing rate by the periodic motions of the chest, and blood pressure can be measured by the delay in pulse arrival time on different body parts and blood oxygen saturation by the intensity ratio of light reflected from skin at two different wavelengths, which indicates the oxygenation levels of the hemoglobin molecule. These vital signs can also be measured by a wearable biometric device, such as a smart watch, and relayed to a central server and to the device. For example a smart watch can provide photoplethysmography (PPG) data signals at a sampling rate of 256 Hz which can be converted to electrocardiography (ECG) signals which can be used to determine subject emotion and diagnose many health problems with very high accuracy. In the infrared domain, an infrared video camera can determine skin temperature which is also correlated with the subject's physiological and psychological state.

The atmosphere also contains many molecular indicators emitted by the subject. Chemical sensors can also be used to analyze the precise chemical composition of odour and environmental pollutant to provide numerous physiological and psychological subject metrics. The rate of perspiration can also be an indicator of subject stress levels and the specific type of biological markers released from the subject skin are closely correlated to the subject state. For example, stress and danger intensifies the odour emitted by the apocrine sweat glands and disease-specific odours produced by breath can be used as olfactory biomarkers of infectious diseases, metabolic diseases and genetic disorders. Gyroscopic motion sensors contained in a smart watch can also be used to determine subject motion and can complement or replace a video camera in the role of deducing subject actions. One or more detection modules can be placed in remote locations or in larger venues to obtain more complete subject coverage. The sensors should be placed in an area free of obstructions and where there is a large field of view to allow the sensors to effectively cover a significant volume of the room. Preferably the remote biometric sensors are provided by a smart watch or wearable worn by the subject, and connected to a processor by a wireless device such as by bluetooth or other wireless technology.

The total amount of essential oils to diffuse depends on environmental conditions. Parameters such as the size of the room, room temperature, humidity, barometric pressure, altitude, and ultraviolet (UV) levels can all contribute to this calculation. For example, small rooms require less essential oils to achieve the same atmospheric concentrations than in larger rooms. Other parameters such as particulate concentration and pollution levels can also play a role in the calculation. Ultrasonic sensors can measure the dimensions of a room. The levels of ambient UV light contribute to determining the decay time of essential oils dispersed in air. Like any other complex molecule, the chemical components of essential oils decompose under UV light. UV light sensors partially determine the time interval between successive releases of the prescription. In this way, intelligent aromatherapy combined with sensor fusion and artificial intelligence can provide a prescription calculated based on the subject's state of health and psychological state in addition to environmental factors and improves over time via sensor feedback and big data modeling. The total amount of essential oils to release can also depend on the sex of the subject because female olfaction is more sensitive than male olfaction. In females, the sense of olfaction is strongest around the time of ovulation necessitating lower prescription doses. (E. Navarrette-Palacios, R. Hudson, G. Reyes-Guerro, R. Guevara-Guzman: 2003, Biological Psychology 63(3), page. 269.) The diagnosis phase can also infer the sex of the subject and can also estimate ovulation time during the female menstrual cycle based on biometric condition data feedback on the aromatherapy treatment.

Neural networks are used to learn the optimum prescription for a subject based on data from the analysis phase. For efficiency reasons a part of these training calculations are performed on a central server and telemetry is used to transmit sensor data and to upload neural weights back to the diffuser device for evaluation. Machine learning is leveraged to predict the future state of a subject and can prescribe a therapy which has the potential to minimize or prevent health issues. The system can thereby automatically learn the subject's behaviour and health patterns, make predictions, and take advanced action to mitigate any health issues. Information obtained during the training of the machine learning algorithm which predicts the future state of a subject is of vital importance to the medical community and could potentially save many lives.

Sensor data for a specific subject is transmitted to a central server for training the machine learning algorithm. The calculated neural weights for that subject are sent back to the device for evaluation. The sensor inputs and calculated neural weights are used to compute the optimum prescription locally on the device. If necessary, the device can operate offline using the most recent neural weights. In addition, sensor data from a plurality of deployed devices can be transmitted to a central server for generalized prescription optimization which can be applied to any subject.

To mitigate against biometric sensor failure the training of the machine learning model can incorporate a simulated random biometric sensor failure using neural dropout to regularize the solution. This decreases the sensitivity of the algorithm to single sensor failure and increases the robustness of the model, which can continue to provide relatively accurate results by leveraging the data from the remaining biometric sensors. This strategy can also mitigate data overfitting, which is a modeling error that occurs when a function is too closely fit to a limited set of data points, thus improving the ability of the model to generalize to novel sensor inputs not encountered during the training phase. Such a scenario might occur if training is performed in non-medical environments and subsequently the device is used in a medical setting which could potentially challenge the algorithm with a much wider range of novel physiological and psychological subject states.

The present system comprising connected one or more Internet-of-Things (IoT) devices can be configured locally at the device, or remotely via mobile app or personalized web site. Biometric and other sensor calibration, diagnostics and initialization procedures can be performed locally or remotely. Additional devices and sensors such as smart watches can be automatically configured from the subject's online account. Once configured, the system can be fully automated and doesn't require any further user interaction, except for essential oil cartridge replacement.

Figure 6A:
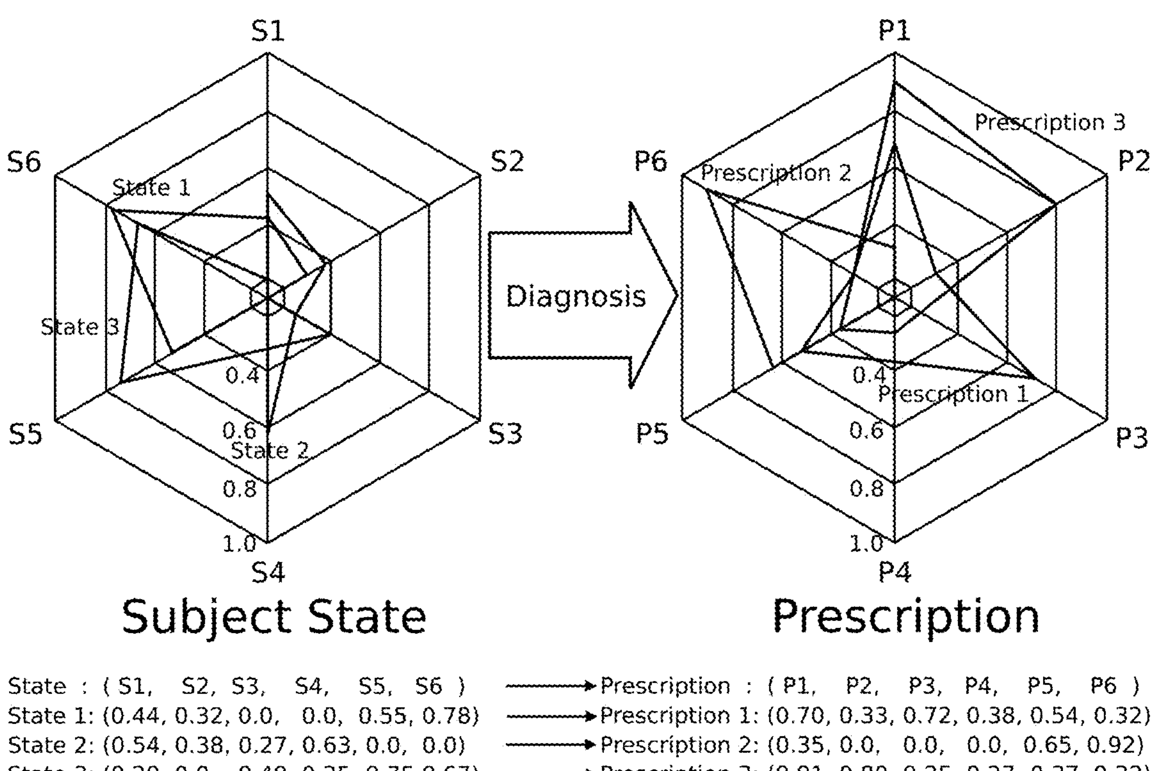
FIG. 6A illustrates the mapping of the subject state to an optimum prescription.

FIG. 6A illustrates the mapping of the subject state to an optimum prescription. In the example shown, three different subject states (State 1, State 2, State 3) corresponding to the normalized values obtained from six subject sensors during the analysis phase are diagnosed and the corresponding prescriptions (Prescription 1, Prescription 2, Prescription 3) are computed as a mixture of six essential oils with different relative weights. The diagnosis of each state provides a prescription for relative amounts of each scent, as well as total amounts of scent for dispense. The diagnosis and prescription algorithms are implemented using machine learning, in particular, a multi-layered neural network whose input neurons are the subject state (S1-S6) and whose output neurons are the relative weights of each essential oil in the prescription (P1-P6). The network is trained to select the optimum prescription based on sensor feedback from the subject.

Figure 6B:
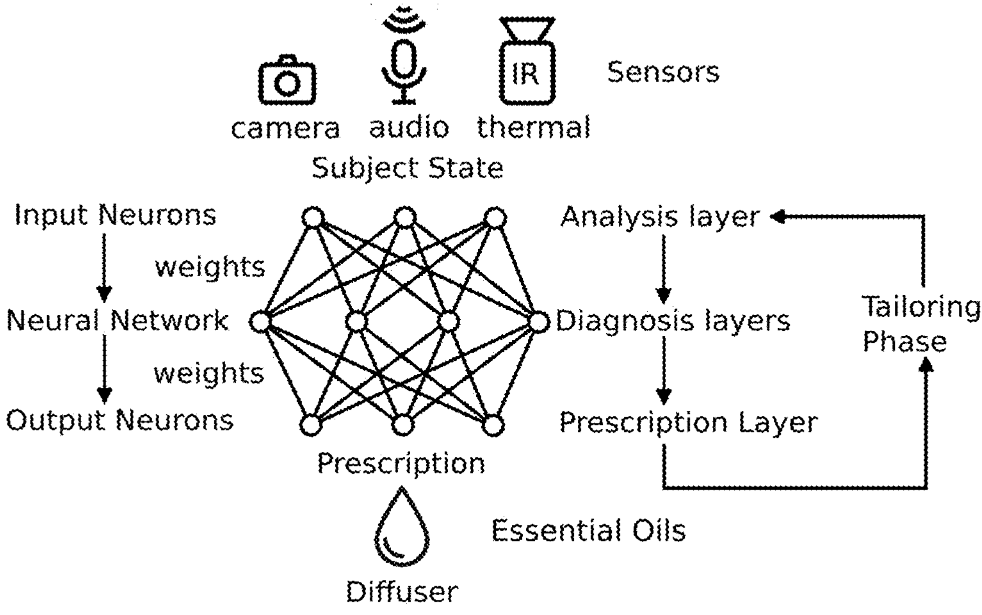
FIG. 6B illustrates how the phases of operation are implemented as various layers in a deep neural network.

FIG. 6B illustrates how the phases of operation are implemented as various layers in a deep neural network illustrates the relationship between the deep neural network and various inputs, outputs and successive phases of operation. The connections between the neurons represent neural weights which are determined during the training. Only three layers and ten neurons are shown to simplify the diagram, however there are many more layers and neurons in the present implementation of a deep neural network. The connections between the components of a system are of critical importance when determining the relationships between components and to predict overall results. Most importantly, a closely coupled system has emergent properties, such as new systemic behaviors not possessed by the individual components. In an analytical view of a system the components are decomposed into a hierarchy where the leaf nodes are fundamental and indicate the physical behavior and properties of each component. However the overall properties of a system as a whole can sometimes be overlooked as focus is placed on examining its parts. In a synthesis approach, which is the one favoured by the present system, the fundamental components of the system are aggregated into a hierarchy of gradually increasing complexity, and the emergent properties and emergent behaviors of the system are deduced and observed. This holistic way of looking at a whole system can reveal new features of the system not present during analysis of individual components. In particular, emergent properties occur when the components are tightly coupled into a system using multiple layers of interpretation based on deep learning algorithms. The present system combines its components into a coherent synthesis to ultimately comprehend the highest level subject states, such as subject emotions and intentions, to provide a course of action to improve their current state and prevent future issues.

From the sensor layer of the analysis phase to the diagnosis phase which contains the correlating layer where subject intent is deduced, a prognosis can be made on potential subject physiological pathology and psychological condition. Most importantly, predictions can be made which support preventative remedial action. The tailoring phase or feedback phase continues to improve the therapy based on careful and continuous monitoring of the subject response to the prescription. In addition, automated prescription optimization performed during the tailoring phase for individual subjects in particular states can be saved anonymously on a server. A sufficiently large data set will rapidly produce a complete scientific mapping of the physiological and psychological benefits of specific essential oils, scents, and their mixtures for a wide variety of subject types, states and conditions. There is a minimum level of complexity required in the interaction of the components of a system to obtain legitimately useful emergent properties. The present system has the minimum threshold above which valuable emergent properties occur, such as the ability to significantly improve and maintain the health of a subject with a high degree of scientific certainty. This scientific research has never been performed before and is an important innovation enabled by the present system.

In use, a prescribing algorithm can be used for analysis, diagnosis, and prescription and tailoring phases to map the subject state to the optimum prescription. In the detection phases, data from a plurality of sensors both on the device and in a wearable biometric measurement device or remote location are used to measure and correlate measured biometric and environmental data using sensor fusion and artificial intelligence in real-time to produce a diagnosis of subject condition such as their physiological health status, mental state and emotional state. Intelligent aromatherapy then personalizes the prescription based on real-time diagnosis of the current state of the subject and synthesizes a large variety of prescriptions using a programmable mixture of a variety essential oils or scents and diffuses the prescription to alleviate the specific condition with high accuracy. Standard aromatherapy requires manually selecting effective therapies through a labour intensive and expensive process of trial and error which must be repeated for each new health problem, however most people don't have the time, patience or expertise to diagnose improvements in their condition corresponding to specific essential oils or mixtures. Through environment sensors, the present system is aware of the exact amounts essential oils to prescribe for the given room dimensions to provide the precise optimum atmospheric concentration to mitigate problems. The system is also aware of the subject's exact state through continuous measurement and analysis of biometric conditions or markers. The tailoring phase continuously adjusts the prescription for the current state of the subject to stimulate or alleviate specific physical or mental conditions. Automatic therapy improvements are implemented by monitoring the subject's response to the prescription in real-time. Dynamic feedback tracks changes in emotions, psychology, physiology, or a combination thereof and provides the optimum prescription specific to the subject and their current state.

The present system also has full control of the release time and relative weight of each essential oil component in the prescription mixture and can orchestrate a dynamic release schedule such that each component is released at a different time. For example, time ordering the component release, for example in order of decreasing volatility, such as top notes first, middle notes second and finally base notes last. This dynamic sequencing or temporal permutation of the aromatherapy recipe reduces olfactory blindness and can simplify the tailoring phase by providing feedback on how the person responds to each component for which they are specialized and is more effective at improving the state of the subject compared to simultaneous release. Alternative mixtures can be permuted with equivalent effects to prevent olfactory blindness or to provide the subject with a choice of which prescription they prefer. Periodic variations in the relative weights of the multiple essential oil components also assists in mitigating olfactory blindness.

Figure 7:
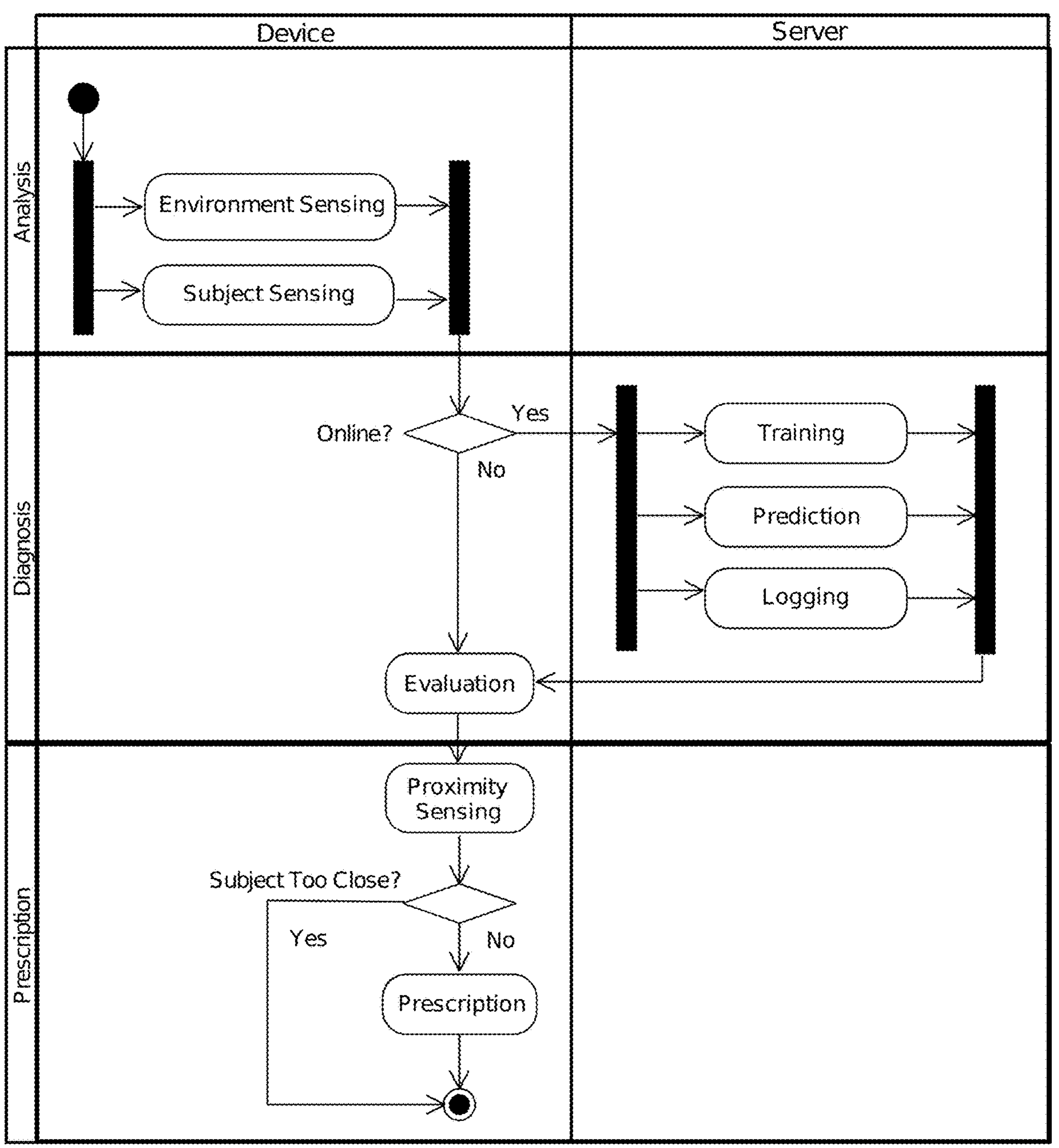
FIG. 7 is an activity diagram illustrating phases of operation of the present system.

FIG. 7 is an activity diagram illustrating phases of operation of the present system including: analysis, diagnosis, and prescription, and the various alternate behaviours if the device goes offline or when the subject is too close to the diffuser. The sensor activities in the analysis phases operate in parallel. After analysis, the training, prediction and logging activities of the diagnosis phase can operate concurrently on the server. If the aromatherapy device goes offline the evaluation activity can continue to operate on previously calculated neural weights. If proximity sensors determine that the subject is too close to the diffuser, the prescription phase can be delayed until the subject moves further away from the device. If the subject is absent, prescriptions halt. The analysis phase measures data points of subject physiological, psychological and environment state in real-time using multiple sensors to reveal a wide range of parameters that impact health and wellness and to provide insight into possible solutions to alleviate conditions and improve their state. Implementation of sensor fusion is done by integrating the various data points into an accurate holistic picture of the subject. With the assistance of machine learning, the diagnosis phase interprets the subject data points provided by the analysis phase to synthesize higher level subject states such as emotion, psychological disorder or medical pathology. Physical biometric conditions and vital signs that can be measured include but are not limited to heart rate, ECG patterns, blood oxygen saturation, body temperature, breathing rate, heart rate variability, body movement, eyelid state, sleep state, facial expressions, subject sounds, speech patterns, and blood pressure. Heart rate variability (HRV) is the physiological phenomenon of variation in the time interval between heartbeats and is measured by the variation in the beat-to-beat interval. Physical attributes can also be either collected using a subject questionnaire or by a biometric sensor and can include but are not limited to daily activity, weight, age, sex, and gender. Medical pathology information can also be collected either by biometric sensor or by subject input regarding, for example, pre-existing conditions, current state of wellness, and baseline health indicators such as body temperature and normal heart function. Using this data, the present apparatus can integrate baseline biometric data and detect the psychological condition of the subject, including but not limited to their state of emotion and arousal intensity, mental state, and physical activity patterns, which can be indicative of psychological disorders such as, for example, depression, bipolar disorder, obsessive compulsive disorder, tic disorders, and others.

Based on the collected data an aromatherapy remedy can be tested to alleviate conditions discovered in the detection phases. Aromatherapies are already known to be successful at, for example, alleviating pain, treating anxiety, relieving stress, reducing nausea, and generally improving wellness. Biometric sensor feedback of the result of the remedy can then be analyzed to adjust the remedy and recipe to optimize for the subject. This tailoring phase monitors the subject response to the prescription phase, automatically improving the therapy and relays this information to a central server for the benefit of other clients. Through long-term monitoring, the tailoring phase can also make predictions about the future state of the subject and can provide a preventative therapy. If the local aromatherapy device goes offline the evaluation can continue to operate on previously calculated neural weights. If proximity sensors determine that the subject is too close to the diffuser, the prescription phase can be delayed until the user moves further away from the device. If the subject is absent or too far away, the prescriptions halt.

Figure 8A:
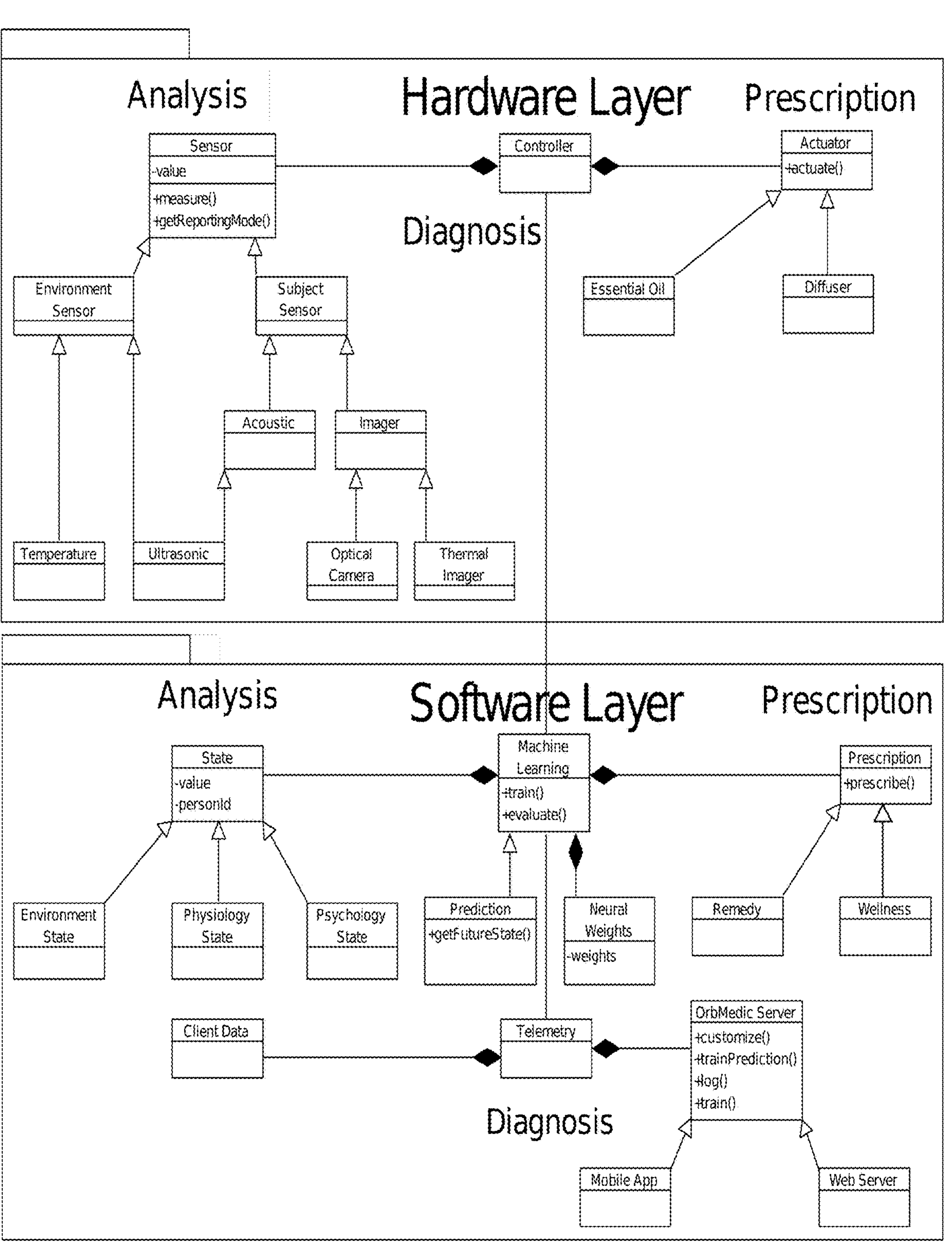
FIG. 8A is a diagram illustrating the correspondence between the low level classes in the hardware layer and the higher levels of abstraction in the software layer.

FIG. 8A is a class diagram illustrating the correspondence between the low level classes in the hardware layer and the higher levels of abstraction in the software layer. The hardware sensor class is partitioned into subject and environment sensor subclasses which corresponds to physiology, psychology and environment state subclasses in the software layer. Analysis sensors in the hardware layer can include but are not limited to environment sensors that sense temperature and take ultrasonic measurements, and subject sensors that can collect, for example acoustic and ultrasonic data, as well as image data through an optical camera or thermal imager. The hardware actuator class controls the essential oil aromatherapy diffuser and corresponds to the prescription class in the higher level software layer. The controller class leverages the machine learning class to perform the analysis/diagnosis step. The machine learning class performs the training and evaluation of the mapping between the state class and the prescription class. The machine learning class holds a reference to the collection of neural weights and also performs state prediction and prediction training. The prescription class is divided into remedy and wellness subclasses which correspond to the remediation or maintenance subject states respectively, such as the environment state, physiology state, and psychology state of the subject. The telemetry class is responsible for distributing the computational load between local and remote resources, remote configuration and alert management. The prescription provides a wellness analysis as well as a prescriptive remedy for the subject.

Figure 8B:
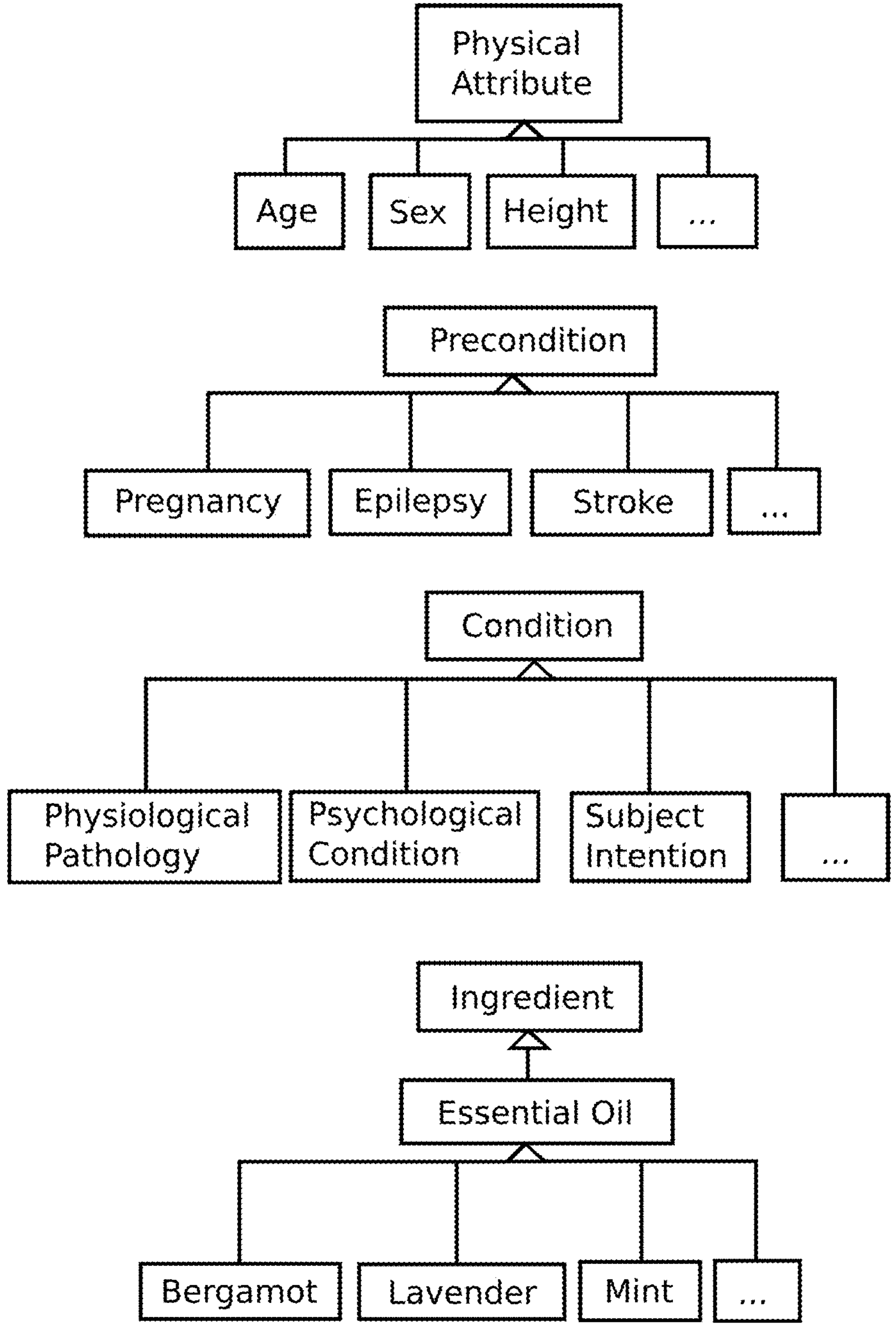
FIG. 8B is a class diagram illustrating the sub-classes of physical attribute, precondition, condition and ingredient/essential oil.

FIG. 8B is a class diagram illustrating the sub-classes of physical attribute, precondition, condition and ingredient/essential oil. Each class and subclass can be incorporated into a subject profile to develop an aromatherapy prescription specific to the subject.

Figure 9:
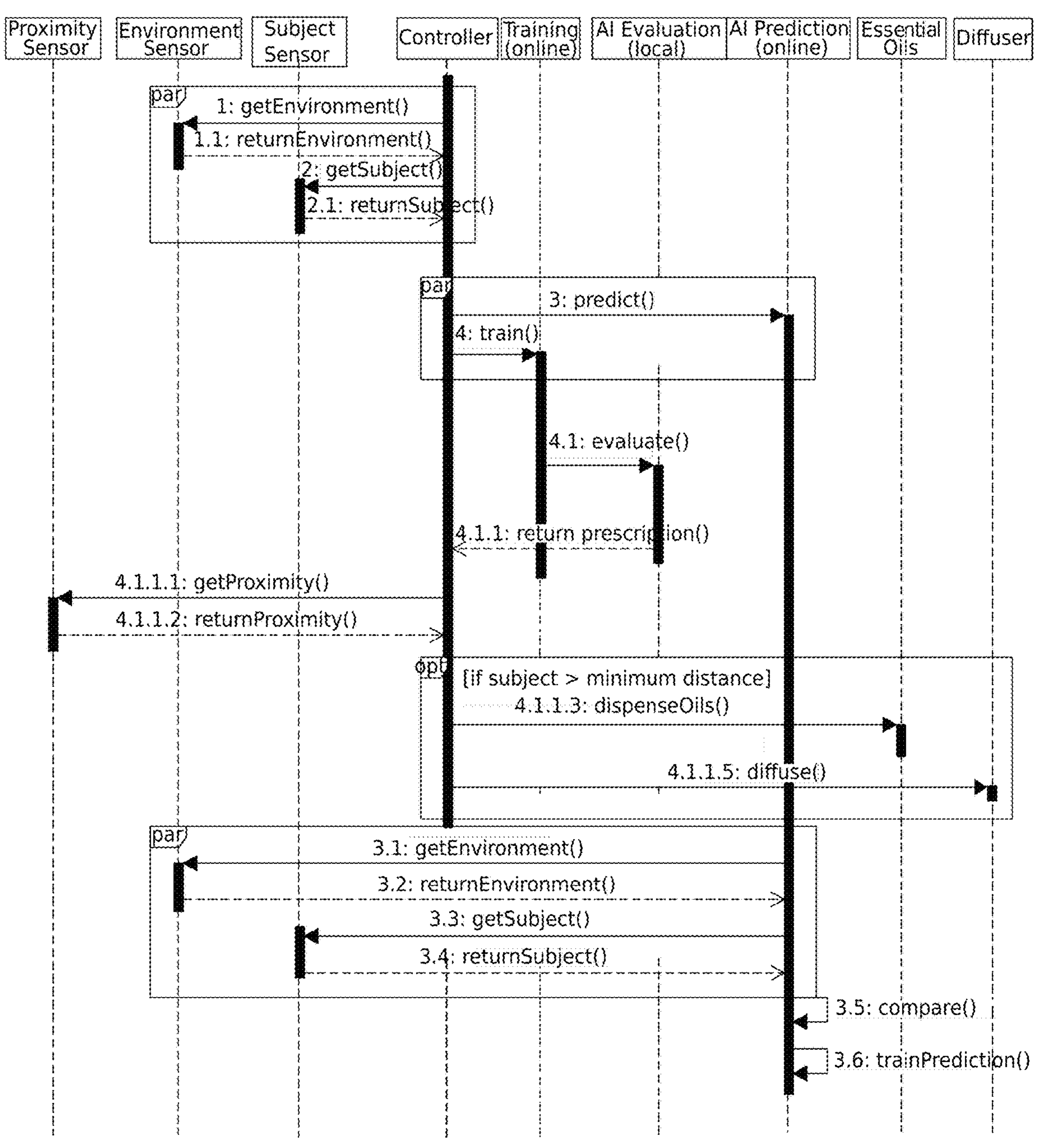
FIG. 9 is a sequence diagram illustrating the time ordering of methods invoked by the hardware controller during normal operation.

FIG. 9 is a sequence diagram illustrating the time ordering of methods invoked by the hardware controller during normal operation. In the analysis phase the environment and subject state is obtained from the sensors in parallel. Next, the diagnosis phase involves the training and evaluation of the machine learning algorithm based on the sensor data. The prescription phase involves the detection of the proximity of the subject and if they are sufficiently far from the diffuser, the creation of a mixture of essential oils using actuators and diffuser. Also included in the diagram is the training of the prediction aspect of the tailoring phase. Intelligent aromatherapy prescribes an optimal mixture of aromatic remedies to release into the air via actuators and a diffuser. The prescription phase makes use of several components each of which constitutes a separate stage in the prescription process. The first component is a proximity sensor which can delay the prescription phase until the subject moves beyond a minimum distance from the diffuser to allow the essential oils to reach final concentration levels in the air. The second component is the individual essential oil dispenser or diffuser apparatus with a cartridge comprising a plurality of scent reservoirs. High purity essential oils or high purity components are preferred in the use of the present apparatus as they have a long shelf life and also delay the decay of airborne mixtures thus increasing the longevity of suspensions. It has been found that pure essential oils remain in suspension longer before degrading when compared to impure essential oils. Both of these effects reduce essential oil purchase frequency thus minimizing recurring costs for the consumer.

The tailoring phase monitors the subject response to the prescription phase and automatically improves the therapy by increasing prescription priority if a positive reaction is detected. This reduces prescription dosage, alters the mixture if a negative reaction is detected, or ceases the therapy if an allergic reaction or medical pre-condition is detected. The subject can optionally tailor the prescription manually for increased effectiveness or simply to choose their preferred prescription among a selection of prescriptions with equivalent mitigating effects. Using continuous monitoring the tailoring phase can further make predictions on future subject states and take preventive therapeutic action. Prediction is a key component in implementing prevention, which is one goal of the present system. From a big data perspective, the amount of knowledge collected during deployment to early adopters offers a unique opportunity to rapidly obtain research results for the most effective prescriptions and to validate the medical efficacy claims of essentials oils. As an internet-of-things device, the present system is equipped with an internet connection to relay the knowledge on prescription improvements back to a central server for the future benefit of all clients. Massive crowd-sourcing of data will lead to more effective prescriptions and provide a firm scientific basis for the legitimate medical claims of essential oils, facilitating United States Food and Drug Administration (FDA) approval of intelligent aromatherapy.

Most research on essential oils and their effects is currently in an immature state with conclusions often relying on ancient, qualitative, or ad-hoc methods. Intelligent aromatherapy revolutionizes this research by approaching the problem scientifically. The present system therefore has a dual role as an intelligent aromatherapy device and as a scientific research instrument. As an IoT device, the present system is a massively distributed sophisticated scientific ecosystem which crowd-sources quantitative data and through artificial intelligence, improves and learns to become more responsive to the needs of clients. From a scientific perspective this democratizes research and development by enabling crowd-sourcing to determine the most effective prescriptions for specific subjects, generic subjects and groups of subjects. Specific mappings between subject state, diagnosis, and appropriate prescription can also be considered valuable intellectual property.

Figure 10:
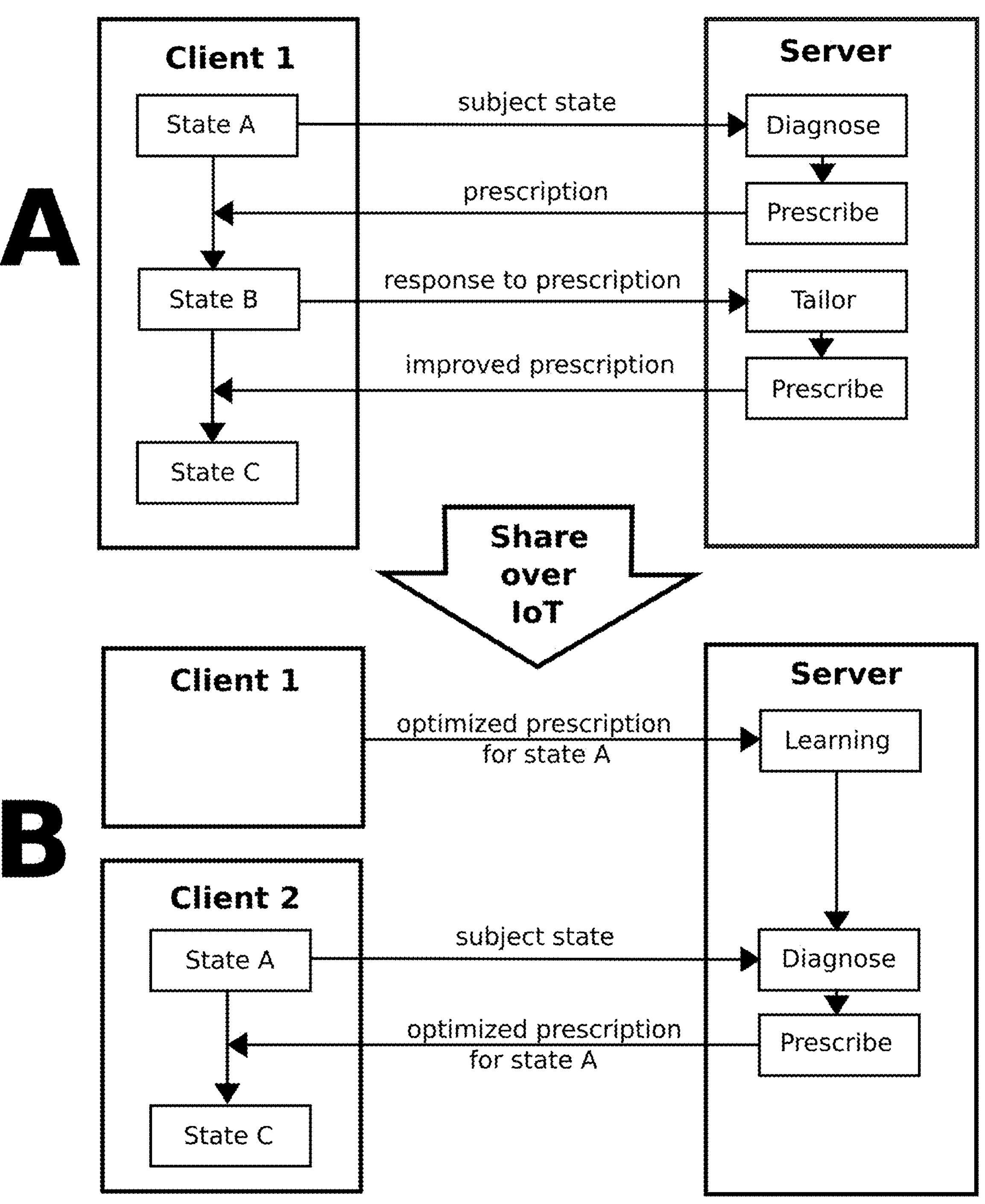
FIG. 10 illustrates one method of crowd-sourcing of the tailoring phase.

FIG. 10 illustrates one method of crowd-sourcing of the tailoring phase. An innovation provided by the present system at the tailoring phase analyzes a subject's response to the prescription for a particular subject state and continuously improves the prescription. The tailoring phase also has the role of generalizing these prescription improvements to be applicable to all subjects in the same particular state and sharing these improvements with all system users using big data techniques. Crowd-sourcing uses internet technologies to collect massive amounts of data points on prescription improvements obtained during the tailoring phase and is the first step in creating a scientifically accurate picture on the effectiveness of prescriptions. Subsequent steps involve big data techniques and deep learning training to optimize prescriptions for mitigating various kinds of conditions in different subjects in various types of states. Optimization occurs firstly on the level of the specific individual and their state, then prescription improvements are classified by the type of individual and after many hierarchical levels of aggregation, prescriptions are progressively generalized for all individuals in the given state. The improvements are continuously fed back into the system to address the real-time needs of specific types of individuals or generic individuals if subject type is unavailable.

Figure 11:
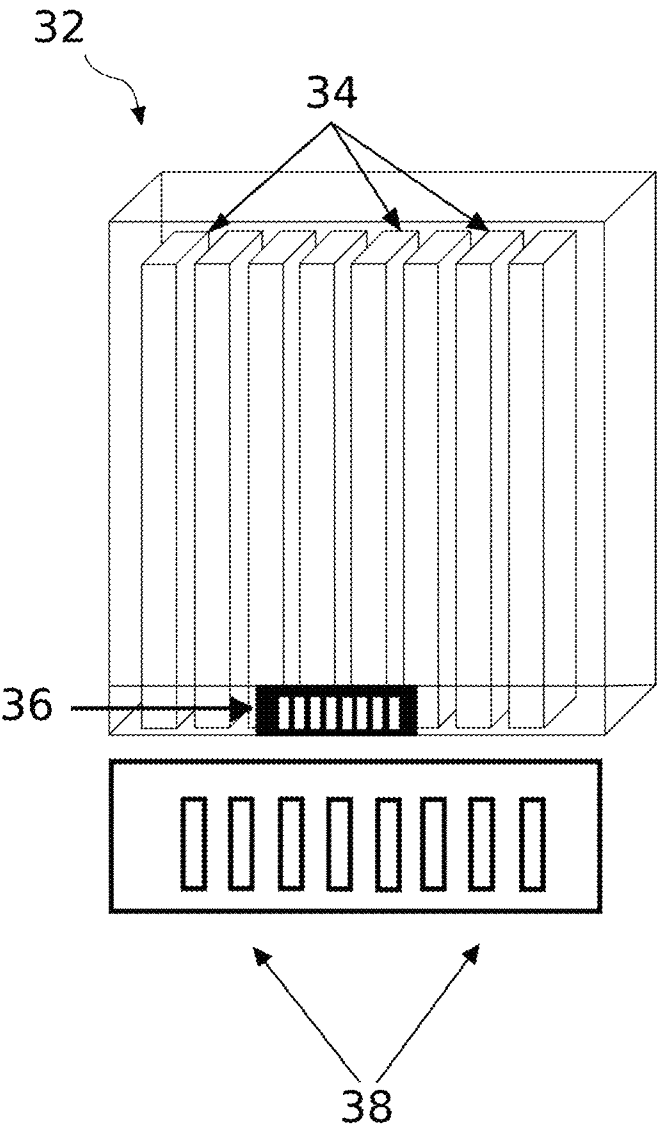
FIG. 11 illustrates an implementation of an aromatherapy cartridge for the described apparatus.

FIG. 11 illustrates an implementation of an aromatherapy cartridge 32 for the described apparatus with eight scent reservoirs 34, however cartridges with 12, 14, 21 or more reservoirs, or different numbers of cartridges, are also feasible. The preferred implementation of the device comprises a plurality of essential oil or scent reservoirs which are located in a cartridge. Each reservoir has an associated actuator which selects a precise contribution from the reservoir 34 to add to the prescription through outlet nozzles 38, and control chip 36 or microcontroller or programmable logic controller (PLC) receives a wired or wireless signal to control the actuators and formulate the aromatherapy recipe. The diffuser releases the prescription into the atmosphere using a thermally controlled low temperature release mechanism, preferably ink-jet printer technology. High temperature diffusion systems can damage the compounds in essential oils rendering them less effective and in some cases harmful by releasing pollutants. Preferably the present apparatus uses a thermally controlled low temperature diffusion system which adapts to the environment and preserves the chemical composition of the mixture, increasing its potency and does not incur any environmental issues. More reservoirs are required in medical environments which are expected to contain subjects with a wider spectrum of subject states and medical conditions which require a larger variety of prescriptions than in the home setting.

The described method and system can be used to provide personalized aromatherapy in real-time using sensors, artificial intelligence and the described diffuser to stimulate or alleviate specific physical or mental conditions for an individual person, where the personalized prescription is automatically sent to the diffuser control system. By measuring the state of a subject through descriptive analytics, diagnostic analytics, and predictive analytics, the diffuser can be provided with an aromatherapy prescription that has been appropriately customized to provide an olfactory environment which improves or maintains the subject's state. This process referred to herein as intelligent aromatherapy, which is a scientifically based, automatic, and quantitative approach to aromatherapy personalization. Therapy can be dispensed on-demand as per subject request or condition, and can be automatically dispensed based on the subject's condition with real time updates to the prescription based on the ADPT sensor fusion and ongoing analytics. In this way therapy can be tailored and changed in real time as the subject condition improves or deteriorates by continuous collection of data on the subject's bio-signal, environment, and social state throughout the therapy to track how the subject responds to the therapy.

Figure 12:
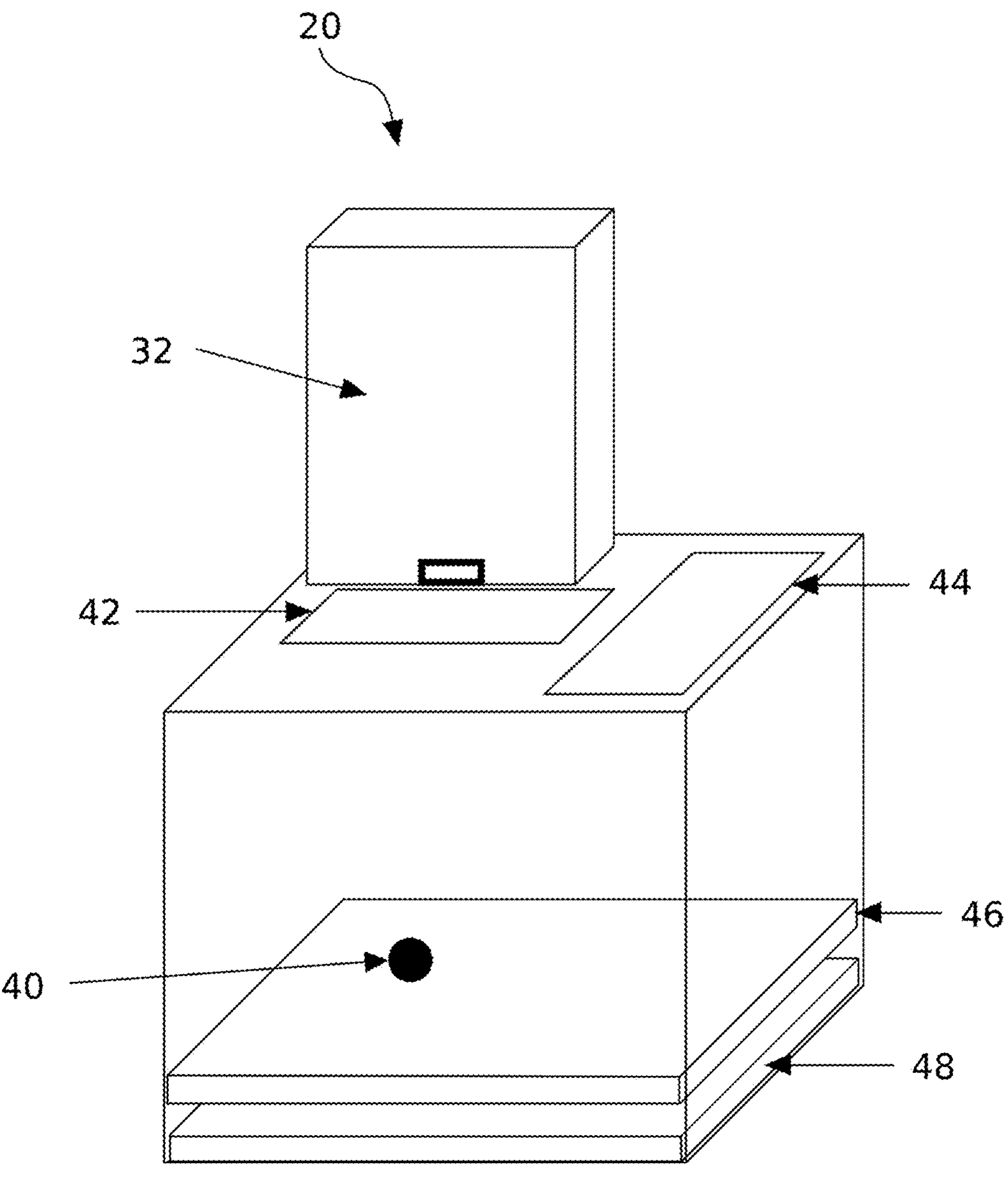
FIG. 12 illustrates an example aromatherapy apparatus for use with the present system.

FIG. 12 illustrates an example aromatherapy apparatus 20 for use with the present system with a dispenser outlet 40 through which the aromatherapy is dispensed. The apparatus comprises a cartridge inlet 42 for receiving a cartridge 32. Multiple reservoirs store essential oils or scents and each reservoir has a dedicated actuator for controlling the release of each scent. A microcontroller is connected to a plurality of actuators and controls each of the dedicated actuators to formulate the blend and amount of oils or scents to be ejected based on a signal received from the control board 46 or PLC. The device preferably also has a display panel 44 to indicate the status of the cartridge such as remaining quantities of essential oils and other measurements or controls. The apparatus also preferably comprises at least one environment sensor such as a camera, ultrasonic sensor, photosensor, thermometer, hygrometer, barometer, UV sensor, chemical sensor or sound sensor. The apparatus can further comprise a speaker to interact with the user. In one case, the apparatus can interact with the user using natural language, to configure the device, warn the subject and even inform paramedics of subject state if subject becomes unconscious. The apparatus can also be programmed to sequence the diffusion of the scent components of a prescription at different times, such as in order of decreasing volatility such as top notes first, middle notes second, and finally base notes. This can assist in reducing olfactory blindness and can simplify the tailoring phase by providing feedback on how each component is mitigating the specific problem for which they are specialized to more effectively improve the state of the subject compare to simultaneous release of all scents at once. The control system in the apparatus comprises an electronic control board to receive wireless commands, for example from Bluetooth™, WiFi, or other internet signal, to select the amount of each scent based on subject emotional health and well-being and instruct a microcontroller to disperse the blend. The apparatus can also optionally comprise mood lights 48 or other lighting.

Figure 13:
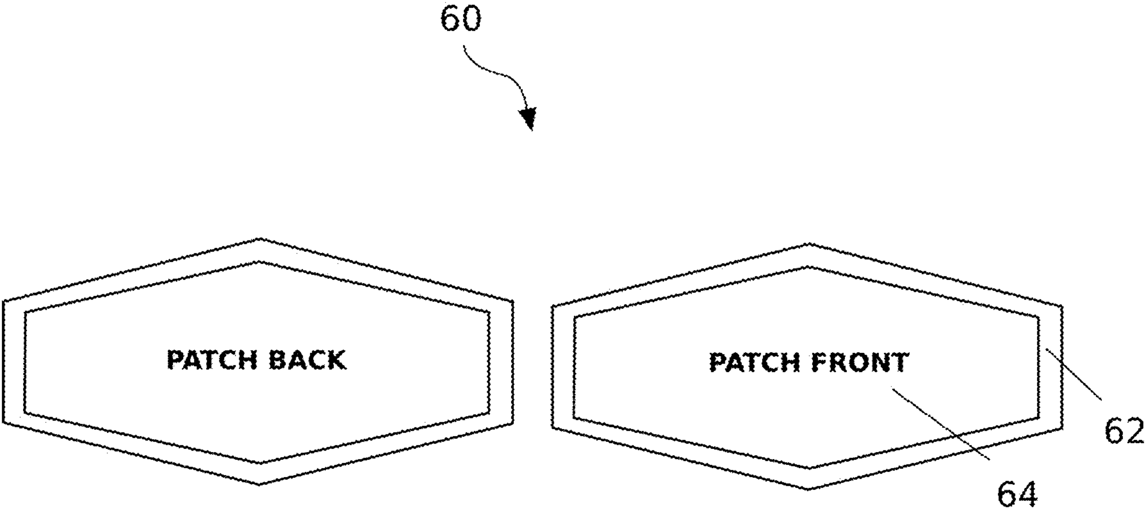
FIG. 13 is an example scent patch which can be used with the present system.

FIG. 13 is an example scent patch 60 which can be used with the present system. Using a scent printer equipped with the same ink-jet technology as the diffuser apparatus, an aromatherapy prescription can also be transferred to a scent patch to be placed near the nose of the subject or on the body, allowing the person to bring the fully personalized scent with them. Using the described system and sensor fusion and artificial intelligence, the system computes an optimum prescription based on subject physical and emotional state and the prescription can be transferred to the porous matrix 64 of a blank scent patch, optionally using ink jet printer technology. The patch has a preferably hypoallergenic adhesive layer 62 protected by a release liner which is peeled off just before applying the patch to the inside of clothing. The patch is preferably located in close proximity to the nose or upper body for more effective inhalation, preferably at the subject shoulder position as higher skin temperature at that location enhances the rate of diffusion and because it is in close proximity to the nose. Body heat assists in the release of aromatherapy molecules from the active layer of the patch and travel outwards away from the skin through the clothing and towards the nose. To minimize irritation, a highly impermeable non-metallic foil can further protects the skin from diffusion of aromatherapy molecules from the active layer. When inhaled, the scent molecules immediately affect the limbic system of the brain. A short time later, some of the molecules can eventually enter the bloodstream via tissues in the lungs. The patches are durable and on a time released schedule which can last for hours. In addition the patches are sanitary and can be disposable for single-use.

In addition to aromatherapy, colour therapy can also be used to provide a therapeutic environment. Three primary colour LEDs such as red, green and blue with varying relative intensities can simulate millions of different colours. Distinct colours can be associated with specific aromatherapies to improve subject condition (also known as 'mood lights'). According to psychology research, acknowledging your emotions is an important step in dealing with them. Each detected human emotion can be mapped to a distinctive colour to inform subjects about their emotional state in real-time. Sound therapy can also be used to provide distinct sounds and music can be associated with specific aromatherapies and/or specific colours to improve subject condition. Human emotions mapped to distinctive sounds can provide emotional feedback. Colour can also be used as a signal from the apparatus to make the user or other person aware of their biometric or emotional state, and a change in stage or different state can be mapped to a distinctive colour to inform subjects in real-time to allow them to be aware of and acknowledge their emotions or change of state.

Figure 14:
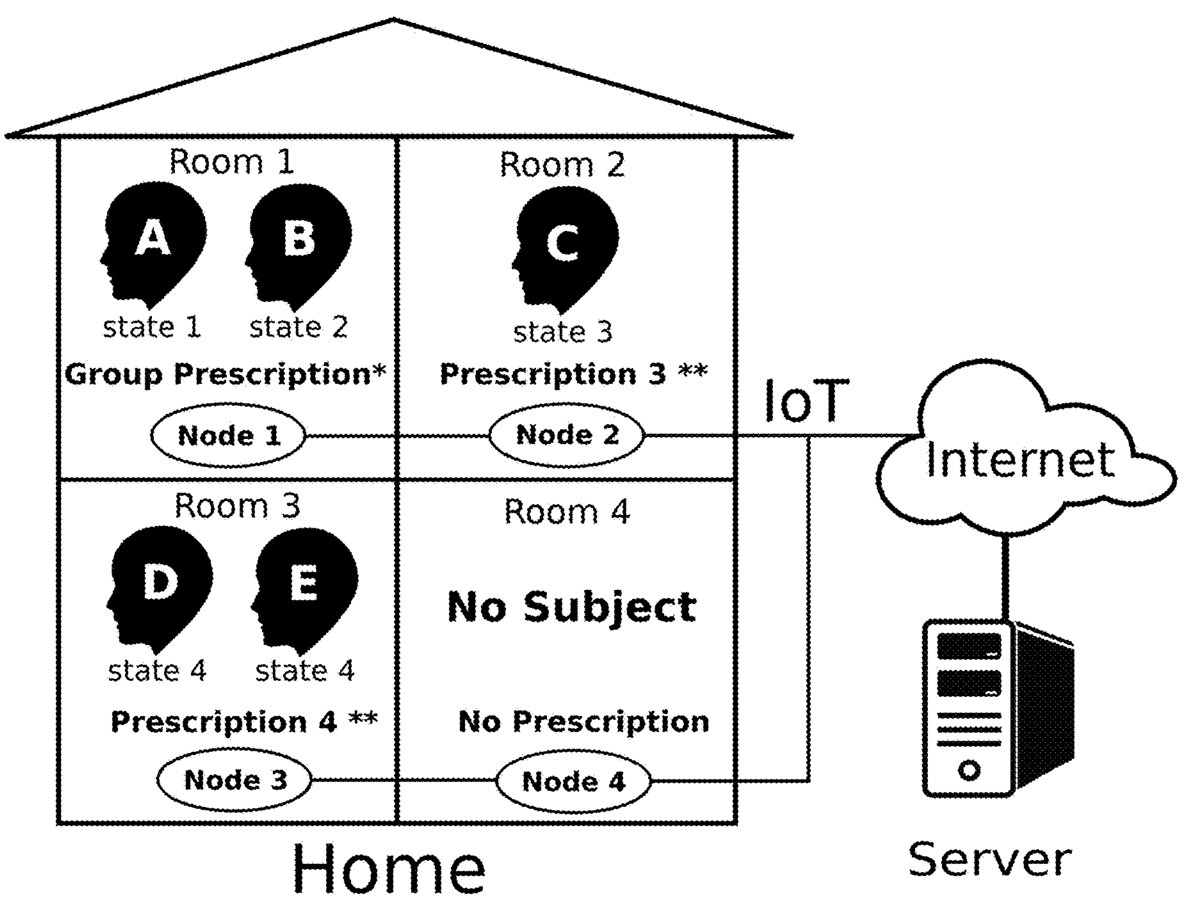
FIG. 14 illustrates a multi-subject prescription model.

FIG. 14 illustrates a multi-subject prescription model. The prescription policy for multiple subjects involves the correlation of the state of each subject to create a group prescription compatible with all the subjects in the room. Each room contains a networked aromatherapy dispenser and zero or more subjects identified as A, B, C, D and E. Each subject is in a particular state such as 1, 2, 3 or 4. For example in room 1, subject A in state 1 is correlated with subject B in state 2 to come up with a group prescription based on consensus. Room 2 contains only one subject (C) in state 3 which can be provided with prescription 3. Room 3 contains subject D and E in state 4 both of which are provided with the same prescription 4. The present system can read biometric data from both subject in the room and calculate an appropriate aromatherapy that will benefit both subjects and avoid exacerbating any pre-condition of either of the subjects. In an example, if one of the subjects in a room has a severe illness, the aromatherapy treatment in the room can be adjusted to a more neutral prescription when other people are in the room who may negatively respond to the aromatherapy. Room 4 contains no subjects and no prescription is required. In addition, the prescription can follow individual subjects as subjects move from room to room because the devices are networked via IoT and communicate subject information between themselves. All prescriptions are adjusted for allergic reactions and preconditions detected in the subject or configured by the subject. Mobile therapy is implemented by transferring the prescription to a scent patch which can continue to deliver the prescription even when the subject is out of range of the diffuser. The calculation of prescription formulation is sensitive to environmental parameters such as the time of day and subject activity. For example, not dispensing in the evening essential oils designed to assist in the awakening of the subject and vice-versa, and not dispensing relaxation or sleep prescriptions at wake-up time. As another example the user may have a preference for aromatherapy not be dispensed during meals. These events and activities do not always occur at fixed times, therefore subject action and subject intention recognition assists in synchronizing appropriate prescription formulations.

Figure 15:
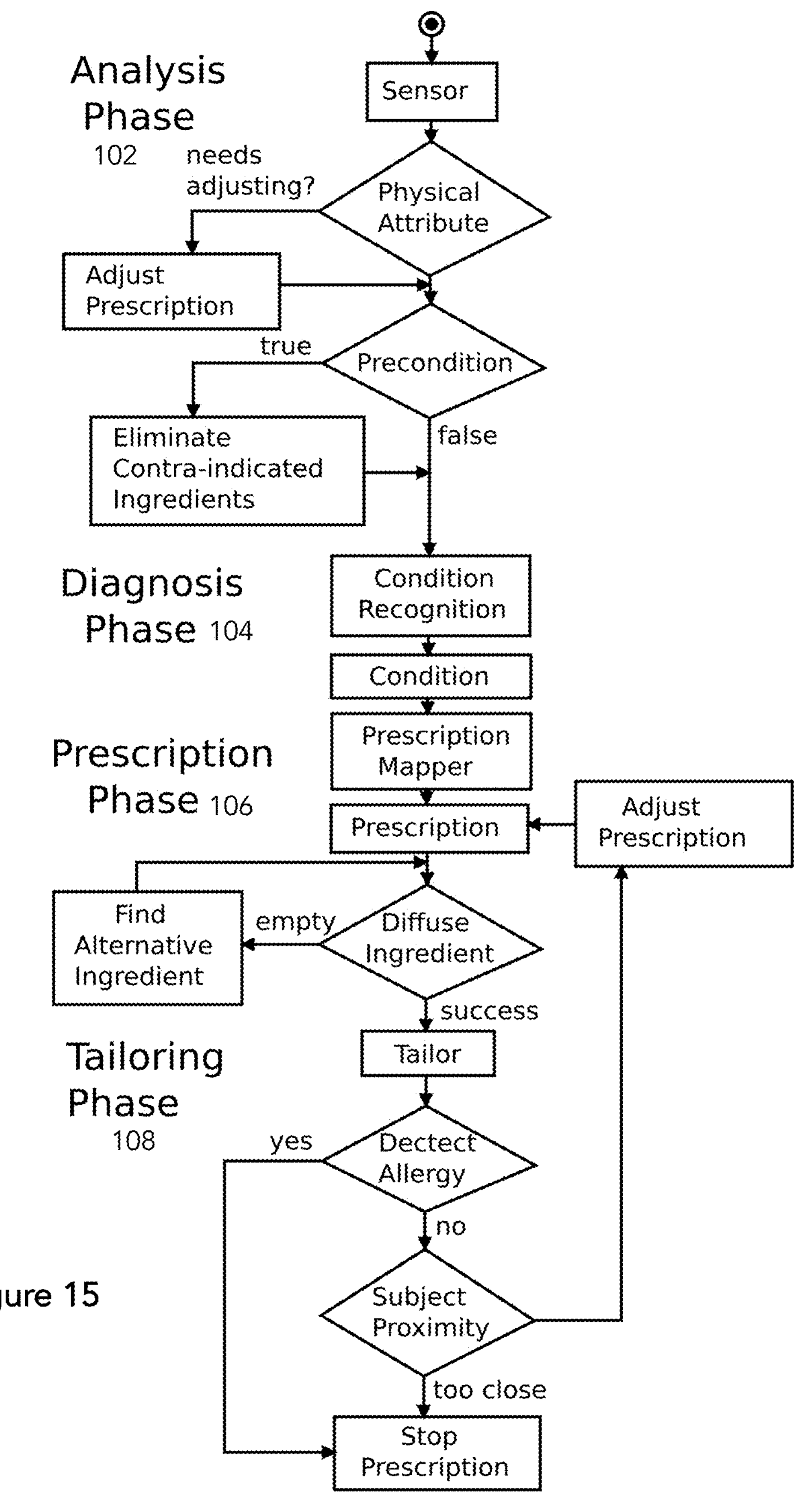
FIG. 15 is a diagnostic decision tree of the present system.

FIG. 15 is a diagnostic decision tree of the present system illustrating in more detail the algorithms used in the various phases and how physical attributes, preconditions and allergies are taken into account. In an analysis phase 102, a sensor reading is taken and a physical attribute is measured by the sensor. If the system determines that the physical attribute or measured biometric requires adjustment, the system will adjust the aromatherapy prescription recommendation. In a diagnosis phase 104, identification of a precondition of the subject can then be evaluated to determine if the new prescription is contra-indicated in any way by the precondition, and the recommended prescription adjusted accordingly in the prescription phase 106. The prescription then takes into account any subject condition and a prescription mapper calculates an appropriate prescription based on the sensed physical attribute of the subject and the precondition. In the tailoring phase, the prescription is diffused. An alternate ingredient mechanism is provided should the device run out of certain essentials oils. In the tailoring phase 108, if an allergy or negative response is detected by the sensor then the prescription is stopped. In addition the system can adjust the prescription based on subject proximity sensing.

Figure 16:
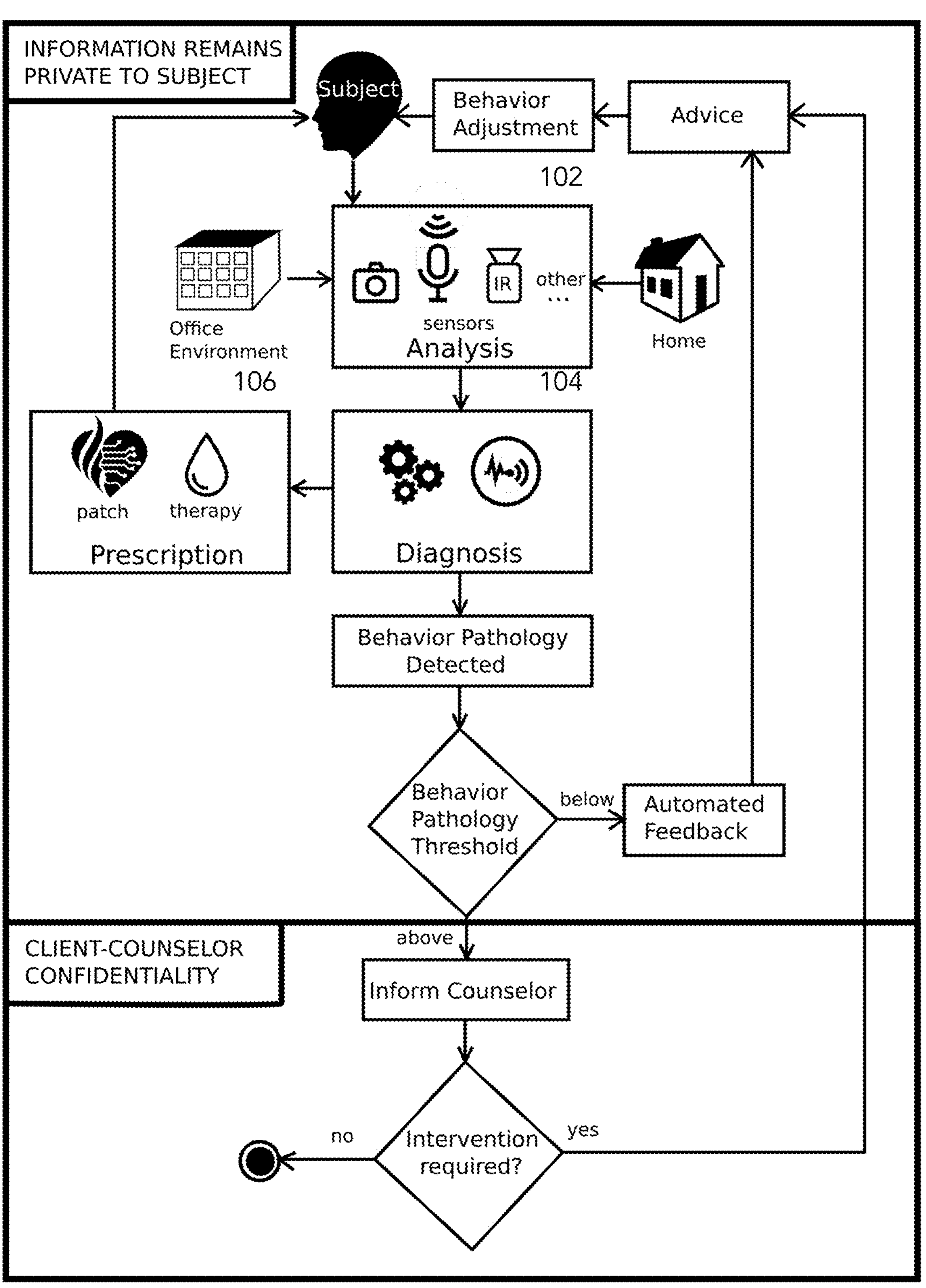
FIG. 16 is a flowchart of an automated prescription combined with behavior self-adjustment through a private automated advice according to an embodiment of the present system.

FIG. 16 is a flowchart of automated prescription combined with behavior self-adjustment through a private automated advice, according to an embodiment of the present system. Through continuous monitoring in an analysis phase 102, behaviour changes or uncharacteristic disruptive behaviour can be detected and mitigated automatically. In addition the subject has the option to be informed of such issues to assist them in learning about and eventually taking action to resolve them. In the diagnosis phase 104 in a workplace, for example, this feature can diagnose toxic environments, unresolved conflicts, interpersonal issues or difficult workplace dynamics. This valuable knowledge has many applications. In one application, a time history of the offending behaviours can be tracked by the subjects involved providing them with advice and the opportunity to correct their behaviour before managers or counsellors are required to intervene if the problem exceeds a given threshold. In another application, a mitigating therapy can be applied to a scent patch worn by the subjects involved. In another application, a mitigating therapy can be released in the homes of the subjects involved. A fully systemic solution to management problems is obtained if all three applications operate concurrently and all deployed devices share their knowledge. In this way, the present system can be an impartial observer of subject state, behaviour and intentions, thus increasing subject privacy by revealing potentially embarrassing results to the subject first, then if issues are not resolved, informing managers and counsellors. Also or alternatively, a prescription phase 106 can provide aromatherapy assistance to the subject to assist with a deteriorating state. This innovation can thereby reduce the management burden with the additional benefit of resolving mental health issues and other health related problems, thus reducing health insurance costs as well.

Experiment 1: Treatment of Anxious Subject

Figure 17A:
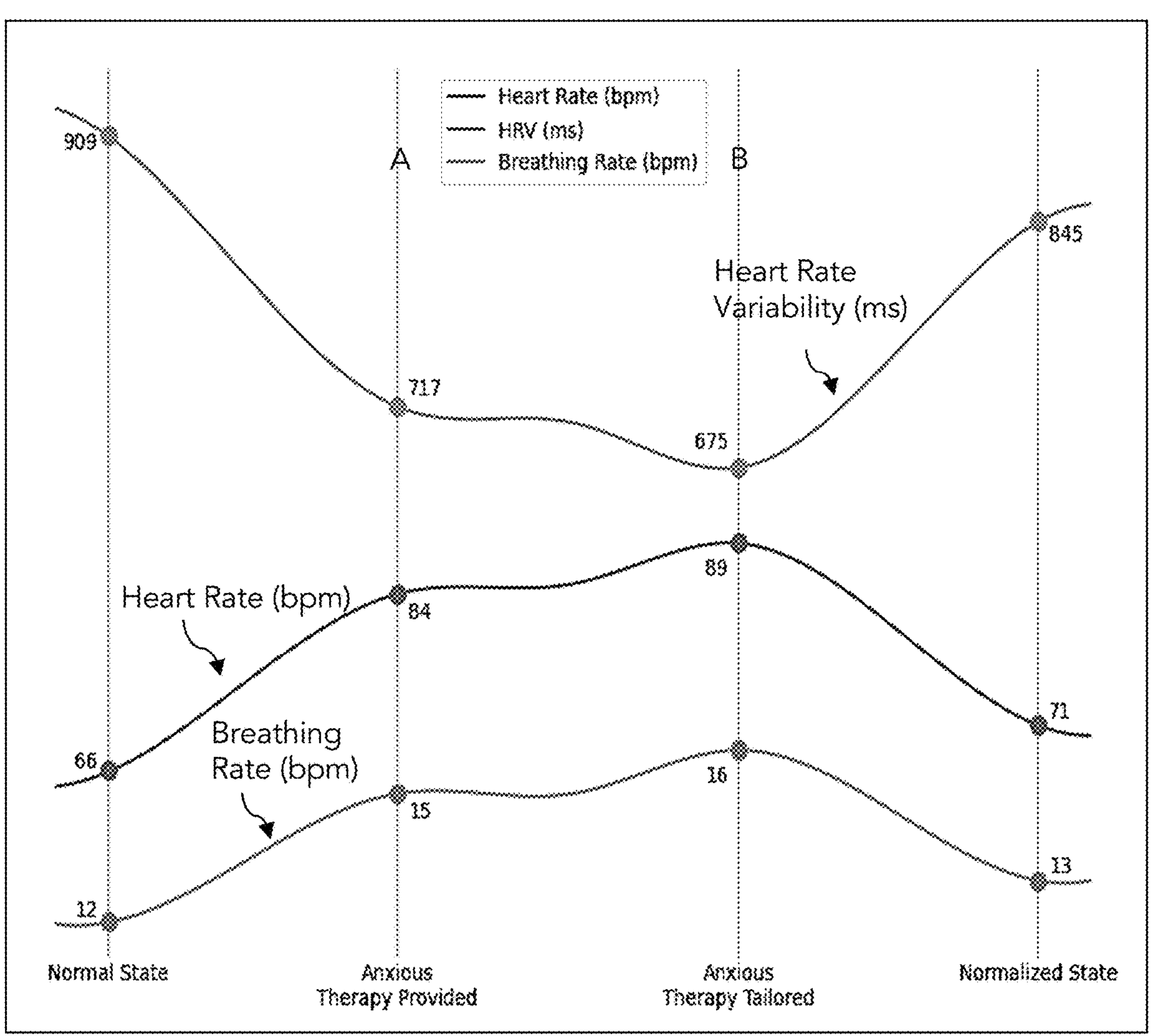
FIG. 17A is a graph of subject data for Experiment 1 including heart rate variability, heart rate, and breathing rate before, during, and after therapy, with a therapy tailoring step.

A non-pregnant female subject (age 36) with diagnosed anxiety was provided aromatherapy treatment according to the described methods and system. Subject data on was collected prior to treatment and the subject was followed to obtain baseline levels on three biometrics heart rate variability (925-833 milliseconds), heart rate (65-70 beats per minute), and breathing rate (12-14 breaths per minute), which includes normal variation prior to the anxious event. FIG. 17A is a graph of subject data including heart rate (beats per minute, bpm), heart rate variability (milliseconds), and breathing rate (breaths per minute) for this subject before, during, and after therapy over time. The graph shows a high anxiety event for the subject where data along the biometrics of heart rate variability, heart rate, and breathing rate significantly deviated from normal baseline for the subject. The data for this event for this subject is shown in Table 1A.

TABLE 1A

| Subject Vitals | | | |
|---|---|---|---|
| | Heart Rate | HRV | Breathing Rate |
| Normal-baseline | 66 bpm | 909 ms | 12 bpm |
| Anxious (time A) (Before Therapy) | 84 bpm | 714 ms | 15 bpm |
| Anxious (time B) (Therapy Tailored) | 89 bpm | 675 ms | 16 bpm |
| Normalized (After Therapy) | 71 bpm | 845 ms | 13 bpm |

Aromatherapy treatment in a first prescription having a first aromatherapy recipe of scents (#05100-876-140) was delivered to treat the anxious state of the subject at time A. The treatment condition of the first prescription is shown in Table 1B and encompasses the regularity, scent intensity, and duration of treatment prescribed for the subject. The aromatherapy treatment or aromatherapy recipe delivered is shown in Table 1C as a permutation in volume in mL delivered from each reservoir in an aromatherapy diffuser based on a scent cartridge with ten scent reservoirs.

TABLE 1B

| Treatment Conditions (RID) | | | |
|---|---|---|---|
| Condition | Regularity | Intensity (1-10) | Duration (minutes) |
| Normal | — | 1 | — |
| Anxious (time A) (Therapy Provided) | 3/Week | 5 | 10-15 |
| Anxious (Aggravated) (time B) (Therapy Tailored) | 1/Week | 8 | 25-30 |
| Normalized (After Therapy) | 3/Week | 1 | — |

TABLE 1C

| Aromatherapy Treatment Delivered (PIP) | | | |
|---|---|---|---|
| | Therapy | | |
| Condition | Permutation (based on a scent cartridge with 10 scent reservoirs) | Intensity (1-10) | Duration (minutes) |
| Normal | — | — | — |
| Anxious (time A) (Therapy provided) | #05100-876-140 (0, 0.23, 0.4, 0, 0.12, 0, 0, 0, 0, 0) mL | 5 | 15 |
| Anxious (Aggravated) (time B) (Therapy Tailored) | #06215-724-379 (0, 0.35, 0.51, 0, 0.19, 0, 0.14, 0, 0, 0.21) mL | 8 | 30 |
| Normalized (After Therapy) | — | — | — |

During and after prescription delivery, biometric data was continued to be collected on the subject on an ongoing basis along the biometric conditions shown. During this time the processor continued to receive the biometric data to determine any change in biometric data and to recalculate and tailor a second aromatherapy prescription for the subject based on the biometric response to the first prescription. At time B, a different and tailored aromatherapy prescription including treatment conditions and delivered aromatherapy recipe (#06215-724-379) was delivered to the subject in a second prescription. The tailored aromatherapy prescription combines subject treatment conditions with the aromatherapy treatment delivered. After delivery of the second tailored prescription at time B, the subject returned, over time, to a healthier state more in line with their biometric normal baseline. The tailored aromatherapy can further be calculated and prescribed one or more times in real time based on biometric and other changes during a therapy session until the subject's condition is stabilized. Successive treatments can also be provided based on the subject's response to the received treatment to further attune the aromatherapy treatment with the subject's needs

Experiment 2: Treatment of Sad Patient

Figure 17B:
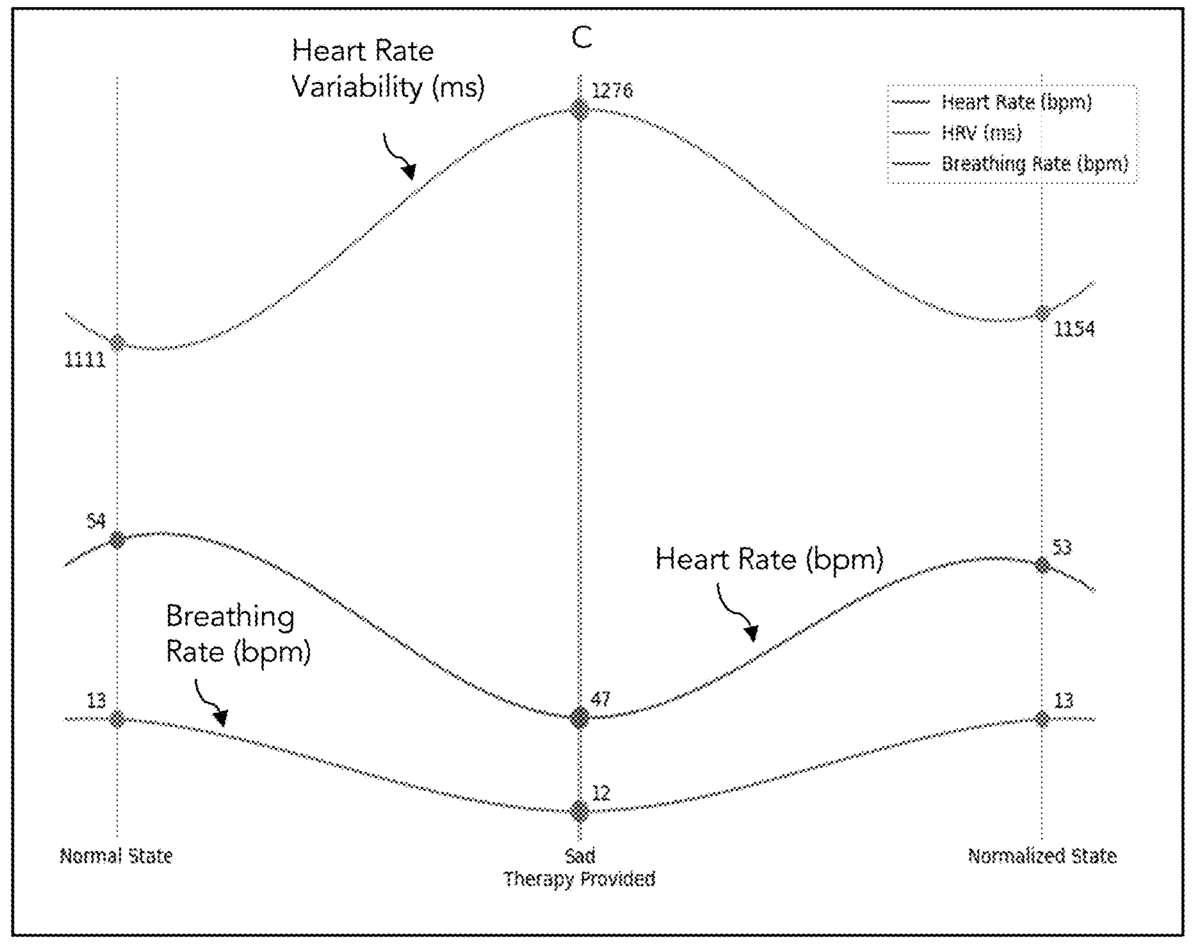
FIG. 17B is a graph of subject data for Experiment 2 including heart rate variability, heart rate, and breathing rate before, during, and after therapy.

A 41-year old male with no known medical pre-conditions was provided with an aromatherapy treatment for general sadness. The subject had a baseline normal heart rate of 52-58 bpm, baseline HRV of 1034-1154 ms, and baseline breathing rate of 12-13 bpm. When the subject experienced and reported sadness, his heart rate was 47 bpm, his HRV rose to 1276 ms, and his breathing rate stayed within normal range. FIG. 17B is a graph of subject data for Experiment 2 including heart rate variability, heart rate, and breathing rate before, during, and after therapy. Tables 2A and 2B provide the treatment conditions and aromatherapy treatment recipe that was given to the subject.

TABLE 2A

| Treatment Conditions (RID) | | | |
|---|---|---|---|
| Condition | Regularity | Intensity (1-10) | Duration (minutes) |
| Normal | — | 1 | — |
| Sad (time C) (Therapy Provided) | 2/Week | 6 | 10-15 |
| Normalized (After Therapy) | 2/Week | 1 | — |

TABLE 2B

| Aromatherapy Treatment Delivered (PIP) | | | |
|---|---|---|---|
| | Therapy | | |
| Condition | Permutation | Intensity (1-10) | Duration (minutes) |
| Normal | — | — | — |
| Sad (time C) (Therapy Provided) | #14753-258-751 (0.31, 0, 0.27, 0, 0, 0.17, 0, 0, 0, 0) mL | 6 | 15 |
| Normalized (After Therapy) | — | — | — |

After treatment the biometric conditions measurements for HRV and heart rate returned to within baseline ranges. Although the experimental data shows the measurement of three biometric conditions, particularly heart rate variability, heart rate, and breathing rate, the present system can use a variety of physiological biometrics, such as vital signs, voice, facial expressions, as well as environmental cues such as weather, room temperature, barometric pressure, subject signals or movements, as well as social state signals such as sleep, physical activity, to identify a subject's psychological state and prescribe an intelligent therapy (aromachology). The ADPT process analyzes all sensor data, diagnoses symptoms using RID (Regularity Intensity Duration), and then prescribes a therapy for that specific emotion using the PIP (Permutation, Precision, and Interval) model. The system continues to follow the subject/user during the therapy session for any changes in their condition.

FIG. 18 is a table providing a non-limiting list of example aromatherapy scents that may be used with the present system and method. Many thousands of plant extracts as well as synthetic scents and aerosolized pharmacologically active compounds are known to provide a therapeutic effect when inhaled or smelled. Each extract and preparation has its own pharmacological properties, and the provided list is only an example set of scents that have been studied and are known as treatments to provide relief for certain ailments. As many scents are used based on their ability to be aerosolized, there is variation in the volatility as well as the degree to which certain individuals experience the aroma, or the aroma or scent strength.

The present intelligent aromatherapy system can find a very broad range of uses for many different subject states in different environments. Aromatherapy can be delivered, for example, in a clinic, at home, or in specially designed delivery pods where people can receive tailored aromatherapy on the go, such as at rest stops, airports, or wherever they are. As a person engages with the present intelligent aromatherapy system a biometric profile can be collected such that the system will learn best treatment protocols to provide given the specific biometric measurements or physiological state that the person is experiencing at the time they seek treatment.

All publications, patents and patent applications mentioned in this specification are indicative of the level of skill of those skilled in the art to which this invention pertains and are herein incorporated by reference. The reference to any prior art in this specification is not, and should not be taken as, an acknowledgement or any form of suggestion that such prior art forms part of the common general knowledge.

The invention being thus described, it will be obvious that the same may be varied in many ways. Such variations are not to be regarded as a departure from the scope of the invention, and all such modifications as would be obvious to one skilled in the art are intended to be included within the scope of the following claims.

The invention claimed is:

1. A system for providing aromatherapy comprising:

a plurality of biometric sensors for measuring biometric data of a subject over time on a plurality of biometric conditions of the subject;

an aromatherapy diffuser for delivering an aromatherapy prescription comprising:

a plurality of scent reservoirs, each scent reservoir comprising an aromatherapy scent; and an electronic control board for controlling a plurality of actuators, each actuator connected to one of the scent reservoirs; and a processor comprising a prescription engine for:

receiving biometric data from the plurality of biometric sensors pertaining to the plurality of biometric conditions of the subject;

combining the biometric data from the plurality of biometric sensors to establish a quantitative model of a physiological state of the subject, the physiological state of the subject being indicative of an emotional state of the subject;

using a prescribing algorithm to prescribe the aromatherapy prescription based on the physiological state of the subject;

receiving updated biometric data from the plurality of biometric sensors to update the physiological state of the subject; and adjusting the aromatherapy prescription to change at least one biometric condition of the subject based on the quantitative model, the processor connected to the electronic control board in the aromatherapy diffuser to provide instructions to the aromatherapy diffuser to deliver the aromatherapy prescription comprising one or more aromatherapy scents from the plurality of scent reservoirs according to a treatment condition for changing the physiological state of the subject.

2. The system of claim 1, wherein the plurality of biometric sensors measure one or more of heart rate, electrocardiogram (ECG), blood oxygen, body temperature, breathing rate, heart rate variability, body movement, sleep state, facial expression, subject sounds, speech patterns, eyelid state, and blood pressure.

3. The system of claim 1, wherein the processor is connected with the internet.

4. The system of claim 1, wherein the aromatherapy prescription comprises a dynamic sequencing of scents over time.

5. The system of claim 1, wherein the treatment condition comprises a regularity, intensity, and duration of treatment.

6. The system of claim 1, wherein the aromatherapy prescription is delivered based on a permutation, interval, and precision process that is specific to the physiological state of the subject, where permutation provides information on what scent or combination of scents to deliver based on the availability in the scent reservoirs, precision is a determination of how much of a particular essential scent or combination of scents to diffuse at a particular time or over a time period, and interval is a determination of how long a particular therapy should be given without producing olfactory blindness.

7. The system of claim 1, wherein the prescription engine dynamically adjusts at least one of regularity, intensity, and duration of diffusion based on a psychological condition of the subject.

8. The system of claim 7, wherein the psychological condition of the subject is determined by one or more of a state of emotion, arousal intensity, mental state, and physical activity pattern.

9. The system of claim 1, wherein the prescription engine is capable of continuously measuring the plurality of biometric conditions and adjusting the aromatherapy prescription in real time based on the biometric data.

10. The system of claim 1, wherein the system further comprises a memory storage device storing a plurality of aromatherapy prescriptions.

11. The system of claim 1, further comprising one or more environmental sensor for measuring environmental data.

12. The system of claim 11, wherein each of the one or more environmental sensor is a camera, thermal camera, ultrasonic sensor, or sound sensor.

13. The system of claim 1, further comprising a microphone configured to recognize speech and wherein the processor performs a text and sentiment analysis to reveal the subject's psychological state.

14. The system of claim 1, wherein the prescribing algorithm incorporates personal data of the subject comprising one or more of gender, sex, age, mass, allergies, preexisting conditions, personal preferences, and current state of wellness.

15. The system of claim 1, wherein the processor is configured to generate predictive alerts of emotional or physiological deterioration using biometric trend analysis.

16. The system of claim 1, wherein the system provides data analytics comprising one or more of reactive analytics, descriptive analytics, proactive analytics, prescriptive analytics, and diagnostic analytics.

17. The system of claim 1, further comprising a vital sign alarm when at least one of the plurality of biometric conditions indicates a concerning state.

18. The system of claim 1, wherein the prescription engine dynamically adjusts the amount of aromatherapy scent delivered from each of the plurality of scent reservoirs based on live biometric data measured by the biometric sensor.

19. The system of claim 1, wherein the prescribing algorithm incorporates a data-based program module that:

continuously analyzes biometric data from the plurality of biometric sensors and the physiological state of the subject to evaluate the efficacy of individual scent combinations;

adapts the aromatherapy prescription using a permutation, precision, and interval model based on prior response patterns; and identifies scent and emotion correlations for the subject and trend detection of other subjects.

* * * * *